(12) United States Patent
Ishikawa et al.

(10) Patent No.: US 10,092,457 B2
(45) Date of Patent: Oct. 9, 2018

(54) UNDERPANTS-TYPE DISPOSABLE DIAPER

(71) Applicant: DAIO PAPER CORPORATION, Ehime (JP)

(72) Inventors: Yasuko Ishikawa, Ehime (JP); Shunji Seno, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 217 days.

(21) Appl. No.: 15/119,627

(22) PCT Filed: Feb. 26, 2015

(86) PCT No.: PCT/JP2015/055558
§ 371 (c)(1),
(2) Date: Aug. 17, 2016

(87) PCT Pub. No.: WO2015/137128
PCT Pub. Date: Sep. 17, 2015

(65) Prior Publication Data
US 2017/0209314 A1     Jul. 27, 2017

(30) Foreign Application Priority Data
Mar. 12, 2014   (JP) ................. 2014-049111

(51) Int. Cl.
*A61F 13/15* (2006.01)
*A61F 13/49* (2006.01)
*A61F 13/496* (2006.01)

(52) U.S. Cl.
CPC .. *A61F 13/49012* (2013.01); *A61F 13/49058* (2013.01); *A61F 13/4963* (2013.01)

(58) Field of Classification Search
CPC .......... A61F 13/49012; A61F 13/49058; A61F 13/4963
(Continued)

(56) References Cited

U.S. PATENT DOCUMENTS

2006/0161130 A1* 7/2006 Zacharias ......... A61F 13/15203
604/385.26
2007/0287975 A1* 12/2007 Fujimoto .......... A61F 13/49011
604/385.3

FOREIGN PATENT DOCUMENTS

JP     4-71922 U     6/1992
JP     2005-287930 A     10/2005
(Continued)

*Primary Examiner* — Jacqueline Stephens
(74) *Attorney, Agent, or Firm* — Muncy, Geissler, Olds & Lowe, P.C.

(57) ABSTRACT

In an underpants-type disposable diaper including a waist edge portion in which pleats extend straight and which has excellent fit, the inner layer and the outer layer at the waist edge portion of an outer body are joined by an adhesive arranged intermittently or a welding process performed intermittently in the width direction and continuously in a direction crossing the width direction, thereby forming sheet joined sections, waist edge portion resilient and elastic members are sandwiched between the inner layer and the outer layer and fixed to at least one of the inner layer and the outer layer at positions intersecting with the sheet joined sections, and the diaper includes an area not being joined and not having resilient and elastic member at an end portion of the outer body on the waist opening side in the waist edge portion, the area not having sheet joined sections nor the waist edge portion resilient and elastic members, and a vertical range being wider than spacing between the waist edge portion resilient and elastic member positioned closest to the waist opening side, and the waist edge portion resilient and elastic member adjacent thereto.

10 Claims, 20 Drawing Sheets

(58) Field of Classification Search
USPC ............ 604/385.24, 385.26, 385.27, 385.29, 604/385.3
See application file for complete search history.

(56) References Cited

FOREIGN PATENT DOCUMENTS

| | | |
|---|---|---|
| JP | 2008-049013 A | 3/2008 |
| JP | 2008-295930 A | 12/2008 |
| JP | 2009-148447 A | 7/2009 |
| JP | 2009-297096 A | 12/2009 |
| JP | 2010-022588 A | 2/2010 |
| JP | 2010-131167 A | 6/2010 |
| JP | 2013-215498 A | 10/2013 |
| JP | 2009-072532 A | 1/2014 |
| WO | WO 2014/010340 A1 | 1/2014 |

\* cited by examiner

FIG. 12 (a)
FIG. 12 (d)
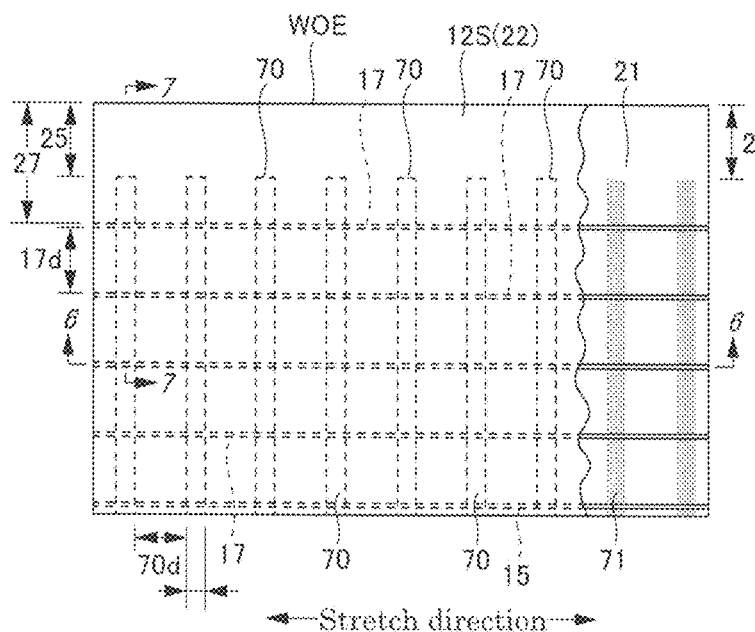
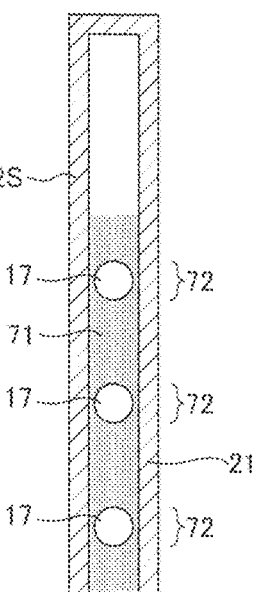
FIG. 12 (b)
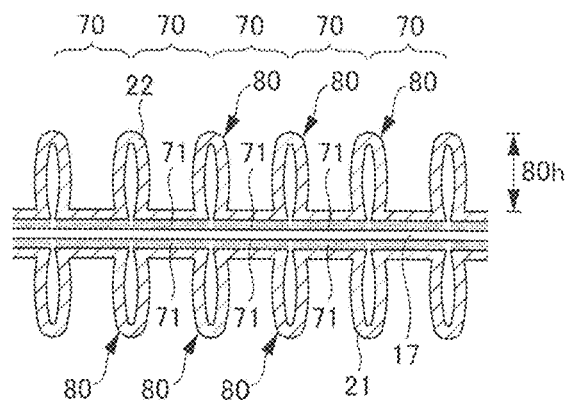
FIG. 12 (c)
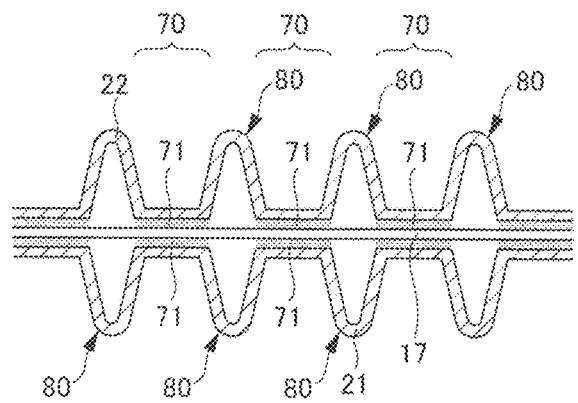

FIG. 18(a)
FIG. 18(d)
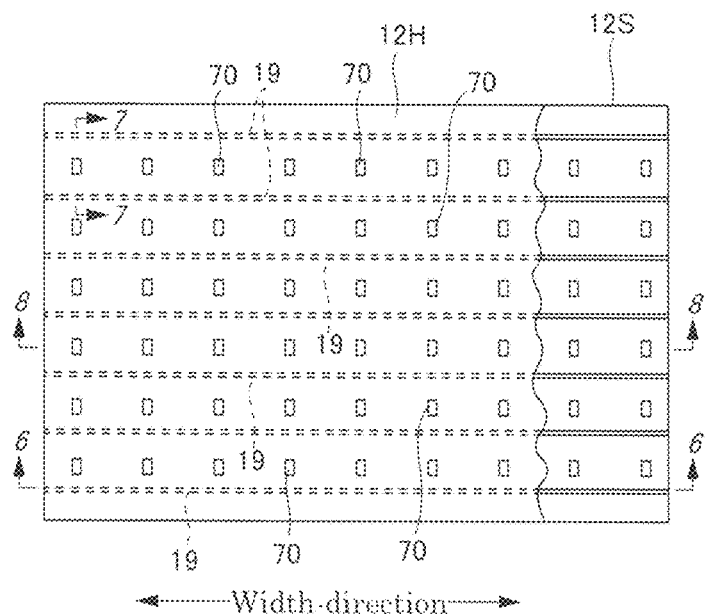
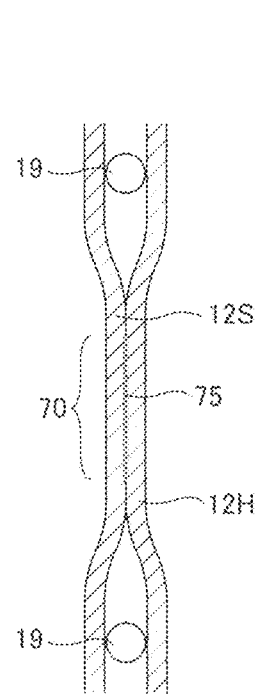
FIG. 18(b)
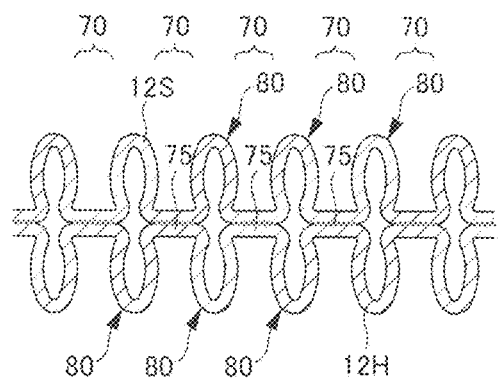
FIG. 18(c)
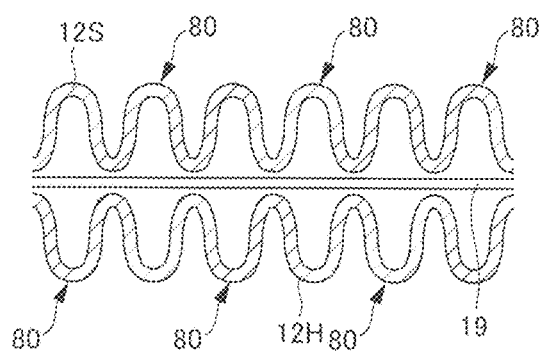

UNDERPANTS-TYPE DISPOSABLE DIAPER

TECHNICAL FIELD

The present invention relates to an underpants-type disposable diaper including a waist edge portion with excellent air permeability and wearing feeling.

BACKGROUND ART

For example, an underpants-type disposable diaper includes an outer body forming a front panel and a back panel, and an inner body that includes an absorber and is fixed to the inner surface of the outer body. The front panel and the back panel of the outer body are joined together at the both sides to form a waist opening and a pair of right and left leg openings.

In the underpants-type disposable diaper, elongated resilient and elastic members such as rubber threads are fixed in an extended state at several sections of the outer body along a circumferential direction to form a stretchable structure along the waist portion to enhance the fit to the human body. In particular, diapers each including waist edge portion resilient and elastic members at the edge portion of the waist opening along the width direction and lower waist portion resilient and elastic members closer to the crotch than to the waist edge portion resilient and elastic members along the width direction are widely used due to their relatively good fit to the human body.

Basically, in such a stretchable structure, the outer body has a multi-layered structure and resilient and elastic members are built-in between layers thereof. The following forms are common in this stretchable structure: a form in which a hot-melt adhesive is applied like a sheet to one of an outer layer facing the outside of and an inner layer facing the inside of the resilient and elastic members to join the outer layer and the inner layer and fix the resilient and elastic members to the outer layer and the inner layer, or a form in which in order to cut down costs by reducing an amount of the hot-melt adhesive to be used or to improve flexibility, the hot-melt adhesive is applied to a peripheral surface over the entire length of the resilient and elastic members which is then sandwiched between the outer layer and the inner layer, thereby joining the outer layer and the inner layer and fixing the resilient and elastic members to the outer layer and the inner layer.

In addition, as an improvement of these stretchable structures, as illustrated in FIG. 18, there have been proposed stretchable structures in which two sheet materials 12H and 12S are intermittently joined together in the width direction and a direction orthogonal to the width direction to form a large number of sheet joined sections 70, and a large number of elongated resilient and elastic members 19 is arranged between the sheet materials 12H and 12S so as not to pass through the sheet joined sections 70 (so as to pass through the non-joined sections) and fix only both end portions of the resilient and elastic members 19 to both sheet materials 12H and 12S (refer to Patent Documents 1 to 3. These stretchable structures will be hereinafter also referred to as vertical intermittent joined form). According to the related art, the vertically aligned sheet joined sections 70 form vertically continuous grooves, and the sections between the grooves form large pleats 80 that swell to the same degree on the both front and back sides. The grooves improve air permeability and the pleats 80 produce excellent softness. Reference sign 75 in FIG. 18 represents a welded portion of the sheet materials 12H and 12S. Even when the sheet joined sections 70 are formed by using an adhesive, shape of the pleats 80 are similar.

However, in the prior-art technology, the pleats make fluffy or wave-shaped pleats. Thus, there is a problem that the diaper is inferior in terms of appearance and air permeability.

In addition, there has also been known formation of a large number of sheet joined sections by bonding two sheet materials intermittently in the width direction and continuously in a direction crossing the width direction (refer to Patent Document 4. The form is hereinafter referred to as a vertical continuous joined form).

However, although the prior art has excellent appearance and air permeability and the pleats extend straight, the prior art has the problems that if it is applied to a stretchable structure of a common waist edge portion where resilient and elastic members are arranged as close as possible to the edge of waist opening, hard sheet joined sections vertically continue to the edge of the waist opening, and that fine contraction wrinkles continue tightly in the vertical direction, thus forming highly rigid wavy concavities and convexities at the edge of the waist opening and deteriorating wearing feeling at the waist edge portion.

CITATION LIST

Patent Document

Patent Document 1: JP-A No. 2008-295930
Patent Document 2: JP-A No. 2009-297096
Patent Document 3: JP-A No. 2009-148447
Patent Document 4: JP-A No. 2010-22588

SUMMARY OF INVENTION

Problems to be Solved by the Invention

A major object of the present invention is to provide an underpants-type disposable diaper including a waist edge portion with excellent air permeability and wearing feeling.

Means for Solving the Problem

The present invention as a solution to the foregoing problem is as follows:
<The Invention of Claim 1>
An underpants-type disposable diaper, including:
an outer body constituting a front panel and a back panel, and an inner body that includes an absorber and is fixed to the inner surface of the outer body, wherein
the front panel of the outer body and the back panel of the outer body are joined together at the both sides to form side seal portions, thereby forming an annular waist portion and a waist opening and a pair of right and left leg openings,
a waist edge portion of the outer body includes a plurality of elongated waist edge portion resilient and elastic members provided along a width direction and separated from each other, an inner layer composed of a sheet material facing the inside of the waist edge portion resilient and elastic members, and an outer layer composed of a sheet material facing the outside of the waist edge portion resilient and elastic members,
the inner layer and the outer layer are joined by an adhesive arranged intermittently or a welding process performed intermittently in the width direction continuously in a direction crossing the width direction, thereby forming sheet joined sections, the waist edge portion resilient and elastic members are fixed to at least one of the inner layer and the outer layer at positions intersecting with the sheet joined sections, the inner layer and the outer layer contracting as the waist edge portion resilient and elastic members contract, portions positioned between the sheet joined sections in the inner layer and the outer layer swell inversely to each other, thus respectively forming pleats, and the diaper includes an area not being joined and not having resilient and elastic member at an end portion of the outer body on the waist opening side in the waist edge portion, the area having no sheet joined sections nor the waist edge portion resilient and elastic members, and a vertical range being wider than spacing between the waist edge portion resilient and elastic member positioned closest to the waist opening side, and the waist edge portion resilient and elastic member adjacent thereto.

(Operation and Effect)

In a conventional underpants-type disposable diaper, there is almost no area not being joined and having no resilient and elastic member at the edge of the waist edge portion on the waist opening side. Consequently, adoption of the vertical continuous joined form at such a waist edge portion causes the problem described above. In contrast, in the present invention, since the area not being joined and having no resilient and elastic member is widely ensured at the edge of the waist opening while adopting the vertical continuous joined form at the waist edge, there is no longer hard sheet joined sections at the end portion on the side of the waist opening, and the contraction wrinkles are larger, sparser, and more flexible than areas having the waist edge portion resilient and elastic members, which thus makes the wearing feeling at the waist edge portion good. Yet, since the waist edge portion of the outer body other than the end portion on the waist opening side takes the vertical continuous joined form, the contraction wrinkles formed at the waist edge portion due to contraction of the waist edge portion resilient and elastic members are formed although they are large and sparse at the end portion of the waist opening side. Thus, air permeability in the vertical direction due to the contraction wrinkles is hardly reduced.

<The Invention of Claim 2>

The underpants-type disposable diaper according to claim 1, wherein distance from the edge of the waist opening to a forward end of the sheet joined section on the waist opening side is 3 to 15 mm, and distance from the edge of the waist opening to the waist edge portion resilient and elastic member positioned closest to the waist opening side is 5 to 20 mm.

(Operation and Effect)

When the distance from the edge of the waist opening to the forward end of the sheet joined section on the waist opening side is less than 3 mm or if the distance from the edge of the waist opening to the waist edge portion resilient and elastic member positioned closest to the waist opening side is less than 5 mm, rigidity of wavy concavities and convexities formed at the edge of the waist opening tends to be high. In addition, it is not preferable that the distance from the edge of the waist opening to the forward end of the sheet joined section on the waist opening side exceeds 15 mm, because wrinkles formed in the area not being joined and having no resilient and elastic member tend to be irregular although the improvement effect of wearing feeling at the waist edge portion remains unchanged. It is also not preferable that the distance from the edge of the waist opening to the waist edge portion resilient and elastic member positioned closest to the waist opening side exceeds 20 mm, because fit at the waist edge portion degrades.

<The Invention of Claim 3>

The underpants-type disposable diaper according to claim 1 or 2, wherein the area not being joined and not having resilient and elastic member has a structure of three or more layers, by folding back at least one of the sheet material constituting the inner layer and the sheet material constituting the outer layer at the waist opening.

(Operation and Effect)

In this manner, when the number of layers of the sheet materials in the area not being joined and having no resilient and elastic member is three or more, volume of the area not being joined and having no resilient and elastic member increases, thus being able to compensate for rigidity without losing flexibility and prevent turn-up at the edge of the waist opening or insufficient formation of contraction wrinkles.

<The Invention of Claim 4>

The underpants-type disposable diaper according to any one of claims 1 to 3, wherein the inner layer and the outer layer are respectively formed by a portion positioned inside and a portion positioned outside one sheet material, which is folded at the waist opening.

(Operation and Effect)

The inner layer and the outer layer being thus formed of the one sheet material, material cost can be reduced.

<The Invention of Claim 5>

The underpants-type disposable diaper according to any one of claims 1 to 4, wherein the sheet joined sections are formed by the adhesive, on the inner layer side and the outer layer side of the waist edge portion resilient and elastic members in parts where the sheet joined sections intersect with the waist edge portion resilient and elastic members, the adhesive is continuous in the direction crossing the width direction, thereby fixing the waist edge portion resilient and elastic members to the inner layer and the outer layer with the adhesive.

(Operation and Effect)

In this manner, the adhesive being continuously present on both the inner layer and the outer layer, the waist edge portion resilient and elastic members can be firmly fixed.

<The Invention of Claim 6>

The underpants-type disposable diaper according to any one of claims 1 to 5, wherein dimension of each sheet joined section in the width direction is 0.5 to 4 mm, and spacing of adjacent sheet joined sections in the width direction is 4 to 8 mm.

(Operation and Effect)

In this manner, based on the vertical continuous joined form, if spacing between adjacent sheet joined sections and dimension of each sheet joined section in the width direction are combined in a specific range, pleats can have both sufficient height and resistance to lying down though the pleats extend straight. The dimension of each sheet joined section in the width direction has an effect on the spacing between adjacent pleats. As with the vertical continuous joined form, if the width exceeds 4 mm when the formed pleats are thin, the spacing between the adjacent pleats is too wide, and individual pleats look independent. In addition, when the pleats are deformed by collapsing and widening, lying down, or the like due to compressive force in a thickness direction, the action of the adjacent pleats supporting each other weakens. Consequently, resistance to deformation or restoration after deformation also weakens, resulting in insufficient softness.

Yet, only setting the dimension of the sheet joined section to 0.5 to 4 mm, and setting the spacing between the adjacent sheet sections to less than 4 mm or over 8 mm result in the following: The spacing between the adjacent sheet joined sections has an effect on height or width of the pleats. When the spacing between the adjacent sheet joined sections is approximately 2 mm, the pleats have poor vertical continuity as with the case in which the pleats are continuously joined in the width direction (thus it makes no sense to intermittently provide sheet joined sections in the width direction). When the spacing between the adjacent sheet joined sections is 3 mm, the action of adjacent pleats supporting each other is not expected although pleats extend straight to the direction orthogonal to the width direction, and softness is short. In addition, when the spacing between the sheet joined sections exceeds 8 mm, the pleats collapse irregularly due to contraction during packing, resulting in poor product appearance. In contrast, only when the width direction dimension of the sheet joined section is set to 0.5 to 4 mm and the spacing between the sheet joined sections is set to 4 to 8 mm, sufficient softness is achieved and the pleats do not easily collapse irregularly due to contraction during packing.

In addition, continuation of the adhesive to form the sheet joined sections in the present invention includes a form in which the adhesive is continuous at any one side and is discontinuous in the direction crossing the width direction at other side since the waist edge resilient and elastic members intervene, in addition to a form in which the adhesive is continuous in the direction crossing the width direction on both the inner layer side and the outer layer side of the waist edge portion resilient and elastic members in the parts where the sheet joined sections intersect with the waist edge portion resilient and elastic members.

In addition, a continuous welding process for forming the sheet joined sections mentioned in the present invention includes as far as a trace of the welding process continues on at least one of the inner layer and the outer layer, not only a form in which the inner layer and the outer layer and the waist edge portion resilient and elastic members are respectively welded and welding continues as the inner layer and the outer layer are indirectly welded, but also a form in which welding between the inner layer and the outer layer does not continue because the waist edge portion resilient and elastic members intervene in the parts where the sheet joined sections intersect with the waist edge portion resilient and elastic members. When sheet joined sections are formed by welding in the vertical continuous joined form, hardening of welded portions is inevitable. However, the effect of hardening is less if the dimension of the sheet joined section falls within the above range. In addition, as a second-order effect, transparency of the welded portions increases and glossy welded portions can achieve stripe-patterned appearance.

In addition, a waist edge portion resilient and elastic members being fixed to a sheet at positions where the waist edge portion resilient and elastic members intersect with sheet joined sections mentioned in the present invention includes not only a form in which the waist edge portion resilient and elastic members and the sheet are bonded (this includes welding in addition to bonding by an adhesive, and applies to the following as well) at the positions where the waist edge portion resilient and elastic members intersect with the sheet joined sections, but also a form in which although the waist edge portion resilient and elastic members and the sheet are not bonded, spacing of the sheet joined sections in the direction crossing the width direction is narrower than thickness of the each waist edge portion resilient and elastic member when it is of natural length, and as a result of the waist edge portion resilient and elastic members being sandwiched between the sheet joined sections and thus fixed, the contraction force of the waist edge portion resilient and elastic members is transferred to the sheet at the positions where the waist edge portion resilient and elastic members intersect with the sheet joined sections. The latter form is a form described in JP-A No. 2008-154998 and JP-A No. 2009-106667, and differs from the form described in Patent Documents 1 to 3 in that a design position of sides of an elastic member passes through a sheet joined section.

<The Invention of Claim 7>

The underpants-type disposable diaper according to any one of claims 1 to 6, wherein spacing of the adjacent waist edge portion resilient and elastic members is 10 mm or less.

(Operation and Effect)

In the case of the present invention, when the spacing of the adjacent waist edge portion resilient and elastic members (not center spacing) exceeds 10 mm, pleat thickness changes in the direction crossing the width direction, and the pleats make fluffy or wave-shaped pleats, although the change is not as much as the vertical intermittent joined form. Therefore, in the present invention, the spacing between the adjacent waist edge portion resilient and elastic members is preferably 10 mm or less.

<The Invention of Claim 8>

The underpants-type disposable diaper according to any one of claims 1 to 7, wherein each of the inner layer and the outer layer is non-woven fabric having thickness of 0.1 to 1 mm and basis weight of 10 to 20 $g/m^2$.

(Operation and Effect)

The present invention is suitable to such an inner layer and an outer layer, in particular.

<The Invention of Claim 9>

The underpants-type disposable diaper according to any one of claims 1 to 8, wherein an extension ratio of the waist edge portion resilient and elastic members when the waist edge portion is completely unfolded in the width direction is 200 to 350%.

(Operation and Effect)

Adoption of such an extension ratio makes the operation and effect of the present invention more significant. Note that the extension ratio means a value when natural length is 100%.

<The Invention of Claim 10>

The underpants-type disposable diaper according to any one of claims 1 to 9, wherein the inner layer and the outer layer are non-woven fabric whose bending resistance in the width direction is higher than that in the direction orthogonal to the width direction.

(Operation and Effect)

Non-woven fabric is suitable as an inner layer and an outer layer. In that case, however, if the bending resistance in the width direction is low, pleats not only have thin and sharp shape but also are easy to lie down. In addition, the compression resilience in the thickness direction is poor. It is possible to increase basis weight of non-woven fabric to improve this, but there is the risk that the diaper may be coarse (excessively enhanced rigidity) and lack softness when touched, although it looks fluffy. Meanwhile, if non-woven fabric whose bending resistance in the width direction is higher than that in the direction orthogonal to the width direction is used for the inner layer and the outer layer, not only pleats easily swell roundly and the compression resilience in the thickness direction is rich, but also the pleats do not lie down easily and yet have rich softness when touched.

Advantageous Effects of Invention

As described above, the present invention produces such advantages that pleats extend straight, and the diaper has excellent softness as well as excellent air permeability and appearance.

BRIEF DESCRIPTION OF THE DRAWINGS

FIG. 6(a) is a planar view in the open state, FIG. 6(b) is a cross-sectional view taken along line 6-6 in a natural length state, FIG. 6(c) is a cross-sectional view taken along line 6-6 in which the stretchable structure is extended to some extent, FIG. 6(d) is a cross-sectional view taken along line 7-7, and FIG. 6(e) is a cross-sectional view corresponding to the cross section taken along line 7-7;

FIGS. 12(a) to (d) illustrate stretchable structures. FIG. 12(a) is a planar view in the open state, FIG. 12(b) is a cross-sectional view taken along line 6-6 in a natural length state, FIG. 12(c) is a cross-sectional view taken along line 6-6 in which the stretchable structure is extended to some extent, and FIG. 12(d) is a cross-sectional view taken along line 7-7;

FIG. 14(a) is a planar view in the open state, FIG. 14(b) is a cross-sectional view taken along line 6-6 in a natural length state, FIG. 14(c) is a cross-sectional view taken along line 6-6 in which the stretchable structure is extended to some extent, and FIG. 14(d) is a cross-sectional view taken along line 7-7;

FIGS. 18(a) to (d) illustrate conventional stretchable structures. FIG. 18(a) is a planar view in the open state, FIG. 18(b) is a cross-sectional view taken along line 6-6 in a natural length state, FIG. 18(c) is a cross-sectional view taken along line 8-8 in the natural length state, and FIG. 18(d) is a cross-sectional view taken along line 7-7;

DESCRIPTION OF EMBODIMENTS

Embodiments of the present invention will be described below with reference to the accompanying drawings.

FIGS. 1 to 8 illustrate one example, the underpants-type disposable diaper 100. The underpants-type disposable diaper 100 is composed of an outer body 12 constituting the outer surface (back surface) of the product and an inner body 200 stuck to the inner surface of the outer body 12. Reference sign Y indicates the entire length of the diaper, and reference sign X indicates the entire width of the diaper.

The inner body 200 is a portion absorbing and retaining excretion and the like such as urine, and the outer body 12 is a portion to be attached to the wearer. The dotted portions in the cross-sectional views indicate joined sections where constituent members are joined together. The joined sections are formed by application of a hot-melt adhesive or the like through solid, bead, curtain, summit, or spiral coating. In the following description, the "front-back direction" refers to the direction linking the ventral side (front side) and the dorsal side (back side), and the "width direction" refers to the direction (right-left direction) orthogonal to the front-back direction. The "up-down direction" refers to the direction that becomes orthogonal to the waist direction when the diaper 100 is worn, that is, when the diaper 100 is folded into two at the crotch portion such that the front panel and the back panel are overlapped at the both sides, in other words, the direction linking a waist opening WO side and a crotch portion side.

(Inner Body)

Figure 3:
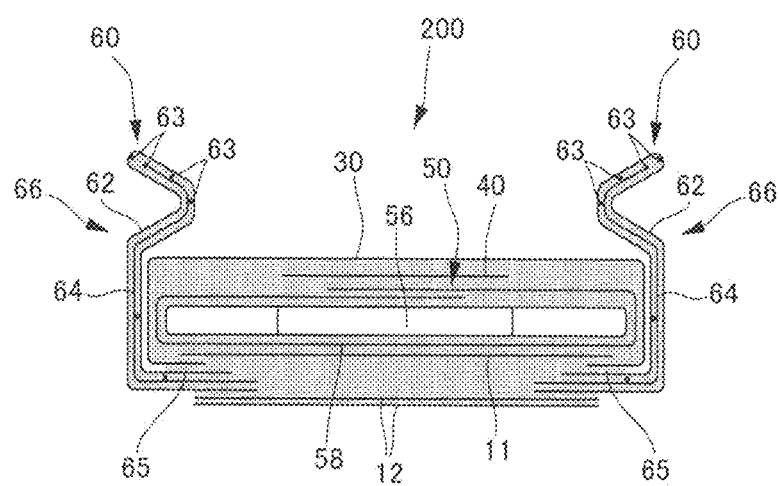
FIG. 3 is a cross-sectional view of FIG. 1 taken along line 3-3.
Figure 4:
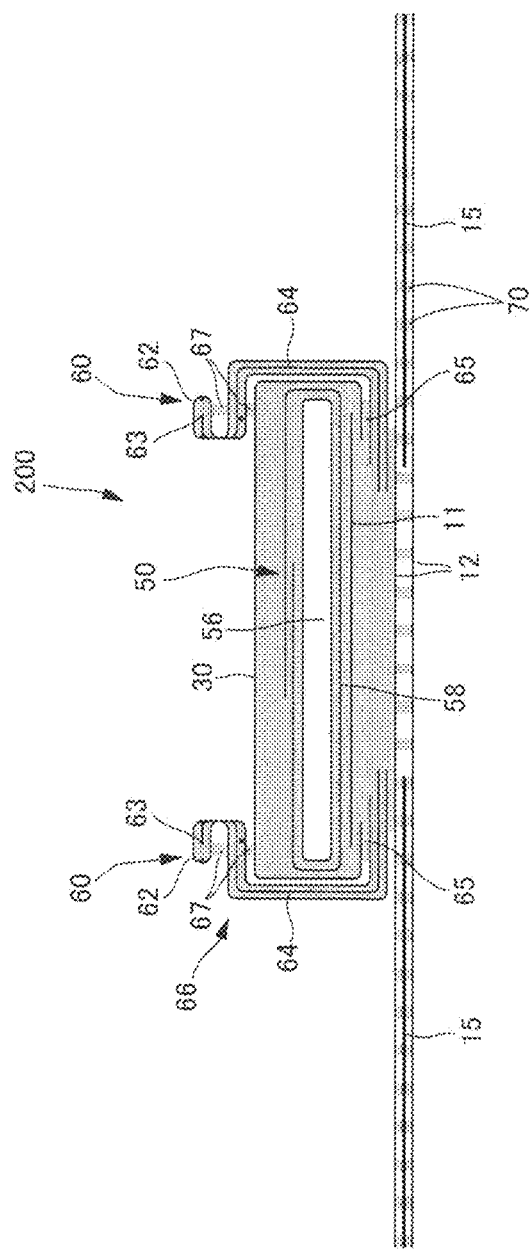
FIG. 4 is a cross-sectional view of FIG. 1 taken along line 4-4.
Figure 5:
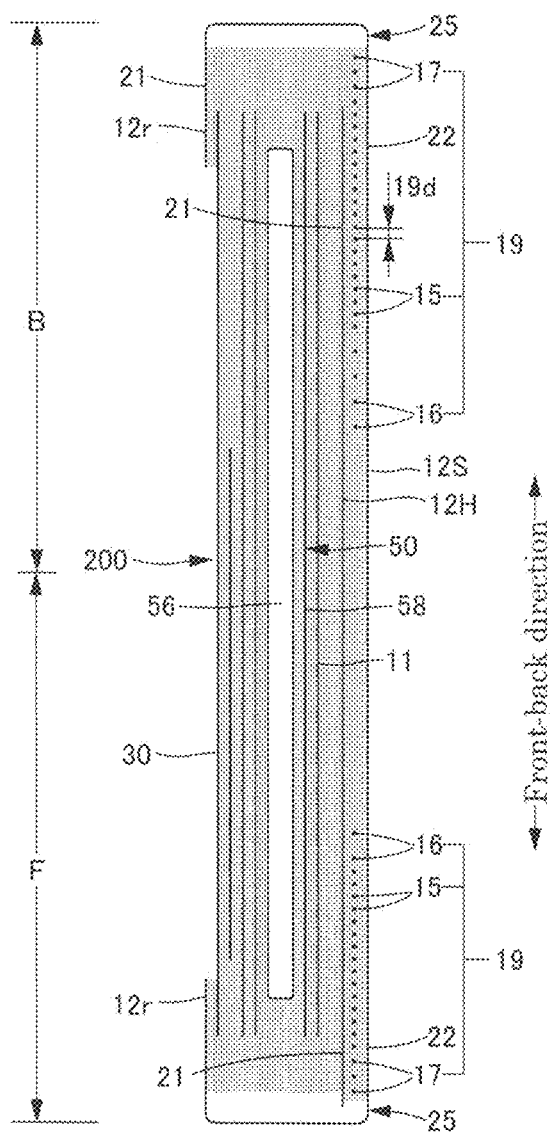
FIG. 5 is a cross-sectional view of FIG. 1 taken along line 5-5.

The inner body 200 may be formed in any shape, although it is rectangular in the illustrated form. The inner body 200 is a main body part with absorptive function that includes a top sheet 30 on the wearer's body side, a liquid impervious sheet 11, and an absorbent element 50 intervening between these sheets, as illustrated in FIGS. 3 to 5. Reference sign 40 indicates an interlayer sheet (second sheet) provided between the top sheet 30 and the absorbent element 50 to move quickly the liquid having passed through the top sheet 30 to the absorbent element 50. Reference sign 60 indicates three-dimensional gathers 60 standing from the both sides of the inner body 200 toward the wearer's body to prevent excretion from leaking toward the both sides of the inner body 200.

(Top Sheet)

The top sheet 30 is pervious to liquid and may be a porous or non-porous non-woven fabric or a porous plastic sheet, for example. There is no specific limitation on raw fibers for the non-woven fabric. For example, the raw fibers may be synthetic fibers based on olefin such as polyethylene and polypropylene, polyester, or polyamide, reproduced fibers of rayon, cupra, or the like, natural fibers of cotton or the like, and mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example. For flexibility and drape properties, spun-bonding and spun-lacing are preferred. For bulkiness and softness, air-through processing, point-bonding, and thermal bonding are preferred.

The top sheet 30 may be composed of a single sheet or a layered sheet obtained by sticking two or more sheets to each other. Similarly, the top sheet 30 may be composed of a single sheet or two or more sheets in a planar direction.

In the case of providing the three-dimensional gathers 60, it is preferred that both sides of the top sheet 30 are extended up to the back side of the absorbent element 50 through between the liquid impervious sheet 11 and the three-dimensional gathers 60, and are adhered to the liquid impervious sheet 11 and the three-dimensional gathers 60 by a hot-melt adhesive or the like to prevent liquid penetration.
(Interlayer Sheet)

To move the liquid having passed through the top sheet 30 quickly to the absorber, the interlayer sheet (also called as "second sheet") 40 higher in liquid permeation speed than the top sheet 30 may be provided. The interlayer sheet 40 can not only move the liquid quickly to the absorber with enhancement in absorption performance of the absorber but also prevent a "reflowing" phenomenon of the absorbed liquid from the absorber to keep the top sheet 30 in a dry state at any time. The interlayer sheet 40 may not be provided.

The interlayer sheet 40 may be made from the same material as that for the top sheet 30, or spun-laced, spun-bonded, SMS, or pulp non-woven fabric, or mixture sheet of pulp and rayon, point-bonded or crape paper, for example. In particular, air-through non-woven fabric is preferred due to its bulkiness. The air-through non-woven fabric preferably uses composite fibers of core-sheath structure. The resin for the core is acceptably polypropylene (PP) but preferably polyester (PET) with high rigidity. The basis weight of the fiber is preferably 20 to 80 g/m$^2$, more preferably 25 to 60 g/m$^2$. The fineness of raw fibers for the non-woven fabric is preferably 2.2 to 10 dtex. To increase the bulk of the non-woven fabric, all or some composite fibers of the raw fibers are preferably eccentric fibers with cores not centered, hollow fibers, or eccentric and hollow fibers.

The interlayer sheet 40 in the illustrated form is centered on an absorber 56 and is narrower than the absorber 56 in the width direction. Alternatively, the interlayer sheet 40 may be provided over the entire width of the absorber 56. The interlayer sheet 40 may be the same in length as the absorber 56, or may be shorter than the absorber 56, falling within the central area for receiving liquid.
(Liquid Impervious Sheet)

There is no particular limitation on the material for the liquid impervious sheet 11. For example, the liquid impervious sheet 11 may be a plastic film made from an olefin resin such as polyethylene and polypropylene, a laminate non-woven fabric with a plastic film on the surface of non-woven fabric, a layered sheet in which non-woven fabric and the like is laid on a plastic film. The liquid impervious sheet 11 is preferably made from a liquid-impervious and moisture-pervious material that has been favorably used in recent years for the viewpoint of prevention of stuffiness. As a widely used moisture-pervious plastic film, there is a microporous plastic film that is obtained by melting and kneading an inorganic filler in an olefin resin such as polyethylene and polypropylene to form a sheet and then elongating the sheet in a uniaxial or biaxial direction. Besides, the liquid impervious sheet 11 may be a non-woven fabric of microdenier fibers, or may be a liquid-impervious sheet that is formed without the use of a plastic film, by enhancing leak-proof performance by reducing the size of gaps between fibers with the application of heat or pressure or by coating the sheet with a high-water absorption resin, a hydrophobic resin, or a water repellent agent.

For enhancement of leak-proof performance, the liquid impervious sheet 11 is preferably extended through the both sides of the absorbent element 50 to the both sides of the absorbent element 50 at the top sheet 30 side. The appropriate width of the extended portion is about 5 to 20 mm at each of the right and left sides.

An excretion indicator changing in color by absorption of liquid may be provided at the inside of the liquid impervious sheet 11, in particular, on the side surface of the absorber 56.
(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. Each of the three-dimensional gathers 60 stands obliquely toward a central portion in the width direction at the base portion, and stands obliquely toward the outside in the width direction from the intermediate portion to the forward edge.

More specifically, each of the three-dimensional gathers 60 is formed such that a belt-like gather sheet 62 having the same length as the length of the inner body 200 in the front-back direction is folded back in two in the width direction, and a plurality of elongated resilient and elastic members 63 is fixed in the extended state along the longitudinal direction with spacing therebetween in the width direction between the sheets at the folded portion and its neighborhood. The end portions of the three-dimensional gathers 60 at the sides opposite to the folded portions in the width direction constitute attachment portions 65 fixed to the back surface of the inner body 200 at the side edges. The portions of the three-dimensional gathers 60 other than the attachment portions 65 constitute protrusions 66 (folded portions) that protrude from the attachment portions 65. The both ends of the protrusions 66 in the front-back direction include base portions that are extended from the attachment portions 65 through the sides of the inner body 200 to the side surfaces of the top sheet 30 and are fixed by front-back fixed portions 67 with a hot-melt adhesive or a heat seal to the side surfaces of the top sheet 30, and edge portions that are folded back from the edges of the base portions toward the outside in the width direction and are fixed to the base portions. The intermediate portions of the protrusions in the front-back direction are non-fixed free portions (inner free portions) to which the elongated resilient and elastic members 63 are fixed in the extended state along the front-back direction.

The gather sheet 62 may be preferably formed by applying a water repellent treatment with silicone or the like as necessary to flexible non-woven fabric excellent in uniformity and concealing performance such as spun-bonded non-woven fabric (SS, SSS, or the like), SMS non-woven fabric (SMS, SSMMS, or the like), and melt-blown non-woven fabric. The basis weight of the fibers is preferably about 10 to 30 g/m$^2$. The elongated resilient and elastic members 63 may be rubber threads or the like. In the case of using spandex rubber threads, the thickness of the threads is preferably 470 to 1240 dtex, more preferably 620 to 940 dtex. The extension ratio of the threads at the time of fixing is preferably 150 to 350%, more preferably 200 to 300%. The "extension ratio" herein takes on a value relative to the natural length as 100%. In addition, a water-proof film 64 may intervene in the gather sheet folded in two as illustrated in the drawing.

The number of elongated resilient and elastic members 63 provided in the free portions of the three-dimensional gathers 60 is preferably two to six, more specifically three to five. The arrangement spacing 60d is appropriately 3 to 10 mm. According to this configuration, the diaper is likely to touch the skin by surface with arrangement of the elongated resilient and elastic members 63. The elongated resilient and elastic members 63 may be arranged not only at the edge portions but also at the base portions.

The attachment portions 65 of the three-dimensional gathers 60 may be fixed to appropriate members in the inner body 200 such as the top sheet 30, the liquid impervious sheet 11, and the absorbent element 50.

In the thus configured three-dimensional gathers 60, the contraction force of the elongated resilient and elastic members 63 acts to make the both end portions in the front-back direction closer to each other. The both end portions of the protrusions 66 in the front-back direction are fixed so as not to stand, whereas the middle portions between the both ends of the protrusions 66 are non-fixed free portions. Accordingly, only the free portions stand to touch the wearer's body as illustrated in FIG. 3. In particular, when the attachment portions 65 are positioned on the back surface of the inner body 200, the three-dimensional gathers 60 stand and open outward in the width direction at the crotch portion and its neighborhood. Accordingly, the three-dimensional gathers 60 are brought into surface contact around the legs to produce an improved fit.

Figure 7:
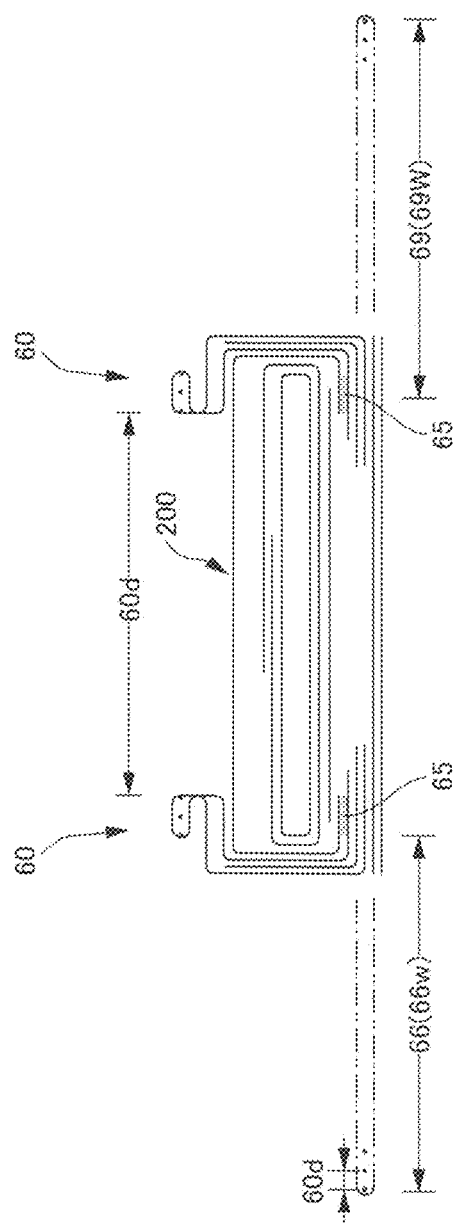
FIG. 7 is a cross-sectional view illustrating only major components of the underpants-type disposable diaper.

The dimensions of the three-dimensional gathers 60 can be decided as appropriate. In the case of a disposable diaper for infants, however, the standing height 66W (width of the protrusions 66 in an open state) is preferably 15 to 60 mm, more specifically 20 to 40 mm as illustrated in FIG. 7, for example. In addition, the separation distance 60d between the folds at the innermost side is preferably 60 to 190 mm, more preferably 70 to 140 mm in the flatly folded state where the three-dimensional gathers 60 are made parallel to the surface of the top sheet 30.

Unlike the illustrated form, the three-dimensional gathers may be provided doubly (in two rows) at each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 may be formed from a fiber assembly. The fiber assembly may be fluff pulp fibers or accumulated short fibers such as synthetic fibers, or a filament assembly obtained by opening tows (fiber bundles) of synthetic fibers such as cellulose acetate, as necessary. The basis weight of fluff pulp or accumulated short fibers may be about 100 to 300 $g/m^2$, and the basis weight of a filament assembly may be about 30 to 120 $g/m^2$, for example. The fineness of synthetic fibers is, for example, 1 to 16 dtex, preferably 1 to 10 dtex, more preferably 1 to 5 dtex. In the case of a filament assembly, the filaments may be non-crimped fibers but are preferably crimped fibers. The number of crimps in the crimped fibers may be, for example, about 5 to 75 per inch, preferably about 10 to 50 per inch, more preferably about 15 to 50 per inch. The crimped fibers are evenly crimped in many cases. High-absorbent polymer particles are preferably dispersed and held in the absorber 56.

Figure 1:
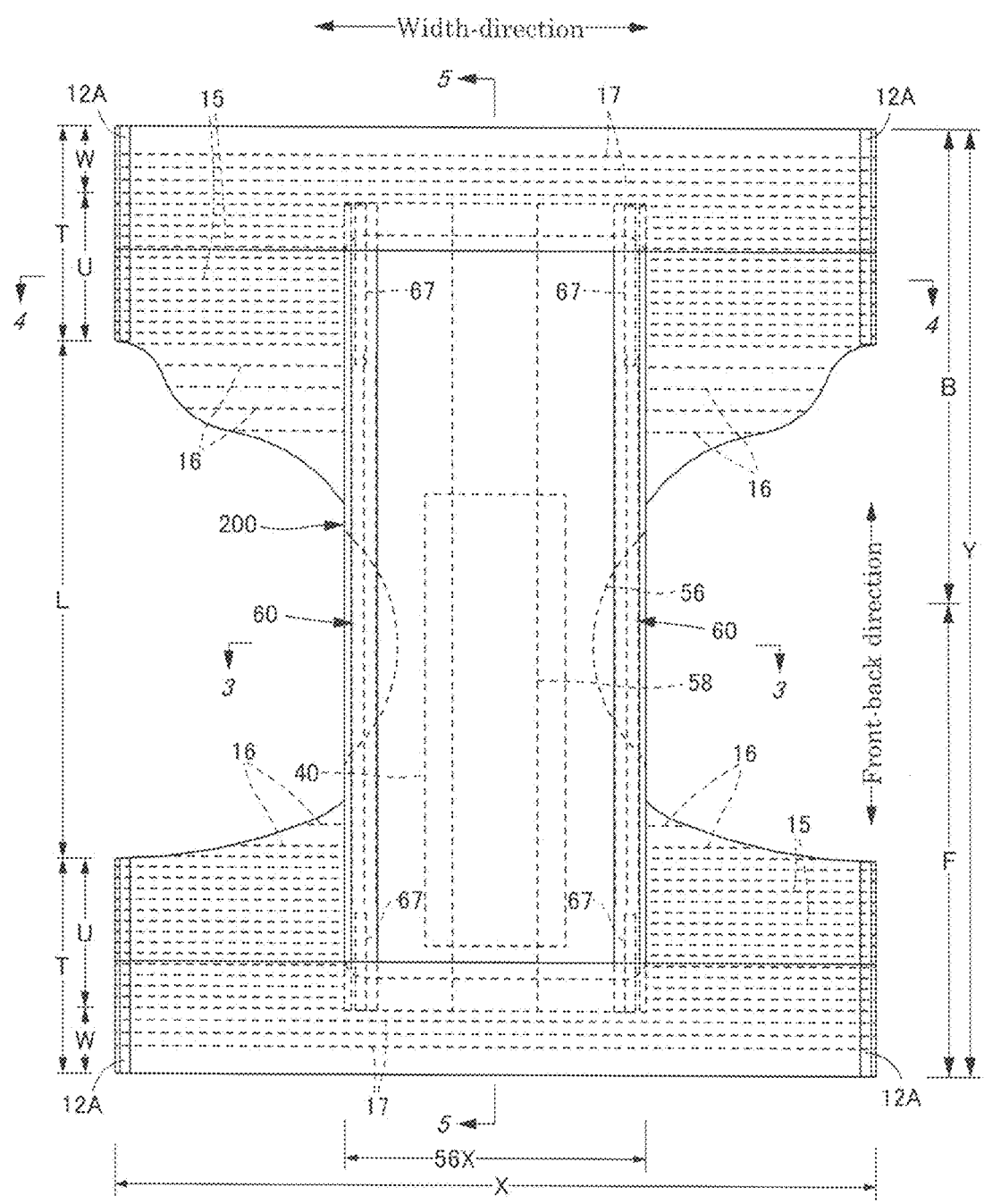
FIG. 1 is a planar view of an inner surface of an underpants-type disposable diaper in the open state.
Figure 2:
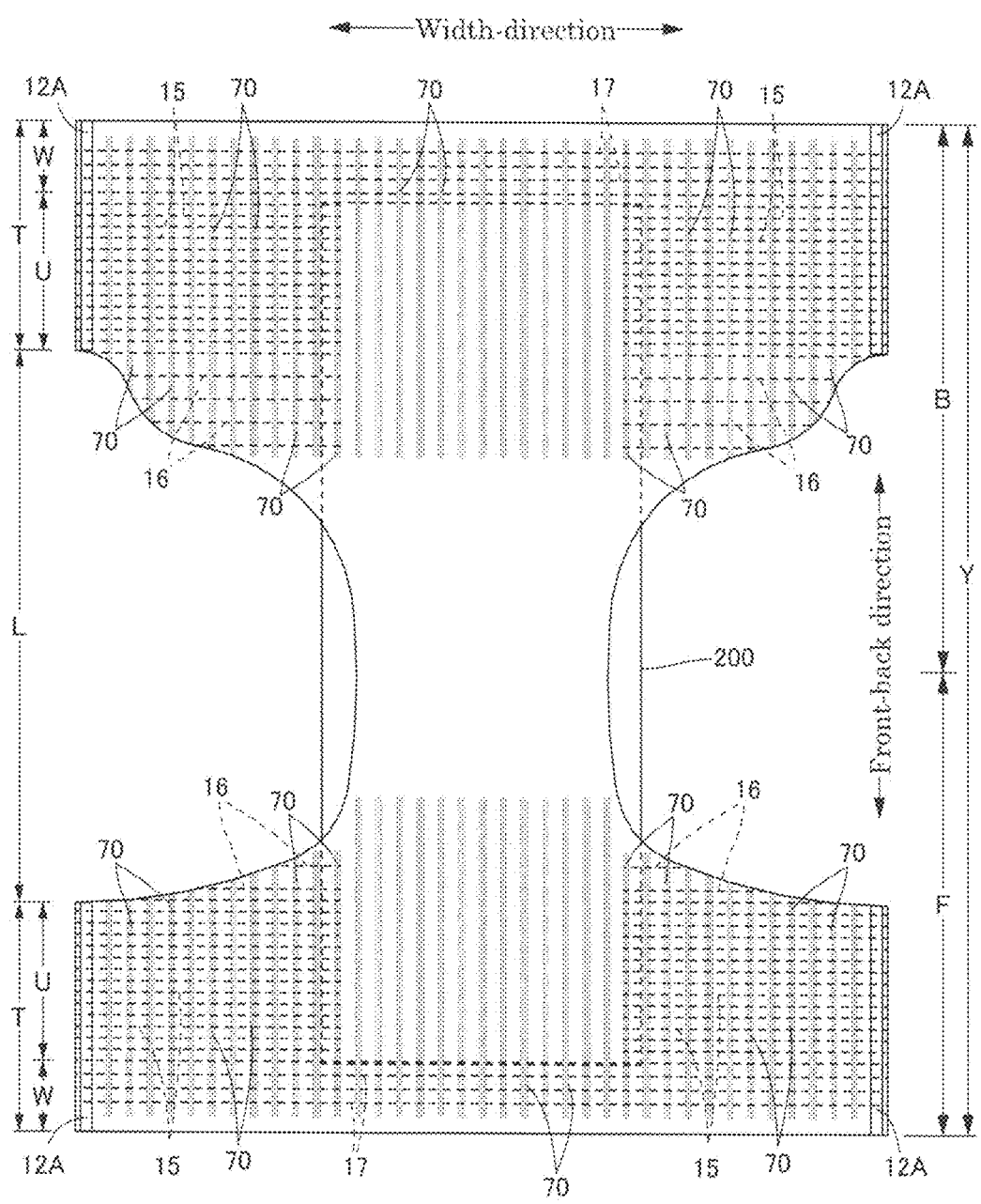
FIG. 2 is a planar view of an outer surface of the underpants-type disposable diaper in the open state.

The absorber 56 may be rectangular in shape but preferably has an hourglass shape having a front end portion, a back end portion, and a narrower portion that is positioned between the front and back end portions and is narrower than the two end portions as illustrated in FIG. 1 to improve the absorber 56 and the three-dimensional gathers 60 in a fit of the edges around the legs.

The dimensions of the absorber can be decided as appropriate. Nevertheless, the absorber preferably extends to the peripheral edges or their neighborhoods of the inner body in the front-back direction and the width direction. Reference sign 56X indicates the width of the absorber 56.

(High-Absorbent Polymer Particles)

The absorber 56 may partially or entirely contain high-absorbent polymer particles. The high-absorbent polymer particles include "powder" as well as "particles". The diameter of the high-absorbent polymer particles may be the same as that of particles for general use in this type of absorbent article, and is desirably 1000 μm or less, in particular 150 to 400 μm. There is no particular limitation on the material for the high-absorbent polymer particles but the material preferably has a water absorption capacity of 40 g/g or more. The high-absorbent polymer particles may be based on starch, cellulose, or synthetic polymer. The high-absorbent polymer particles may be made of a starch-acrylate graft copolymer, a saponified material of starch-acrylonitrile copolymer, a crosslinking substance of carboxymethyl-cellulose sodium, an acrylate polymer, or the like. The high-absorbent polymer particles are preferably used in a general particulate form but may be used in another form.

The water absorption rate of the high-absorbent polymer particles is preferably 40 seconds or less. At a water absorption rate of more than 40 seconds, the absorbed liquid is more likely to flow back from the absorber 56 to the outside of the absorber 56 (so called "reflowing").

The gel strength of the high-absorbent polymer particles is preferably 1000 Pa or more. Accordingly, it is possible to suppress effectively stickiness of the absorber after liquid absorption even when the absorber 56 is of high bulk.

The basis weight of the high absorbent polymer particles can be decided as appropriate depending on the absorption volume required in the use of the absorber 56. Therefore, although being not specified absolutely, the basis weight may be 50 to 350 $g/m^2$. When the basis weight of the polymer is lower than 50 $g/m^2$, it is hard to assure the absorption volume. When the basis weight of the polymer exceeds 350 $g/m^2$, the effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion region than the other regions. With regard to gender differences, the dispersing density (quantity) of the high-absorbent polymer particles may be increased at the front side of the product for male, and may be increased at the central part of the product for female. In addition, the polymer may not be provided locally (in spots for example) in the absorber 56 in the planar direction.

(Wrapping Sheet)

In the case of using the wrapping sheet 58, the material thereof may be tissue paper, in particular, crape paper, non-woven fabric, polyethylene-laminated non-woven fabric, a porous sheet, or the like. However, the material sheet is desirably configured to retain the high-absorbent polymer particles. In the case of using non-woven fabric instead of crape paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m², in particular 10 to 30 g/m².

The form of wrapping by the wrapping sheet 58 can be decided as appropriate. Nevertheless, from the viewpoint of ease of producing and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back edges extended off from the upper side surface and under side surface of the absorber 56 so that the extended portions are crushed in the upper side-under side direction and joined together by a joint means such as a hot-melt adhesive.

(Outer Body)

Figure 8:
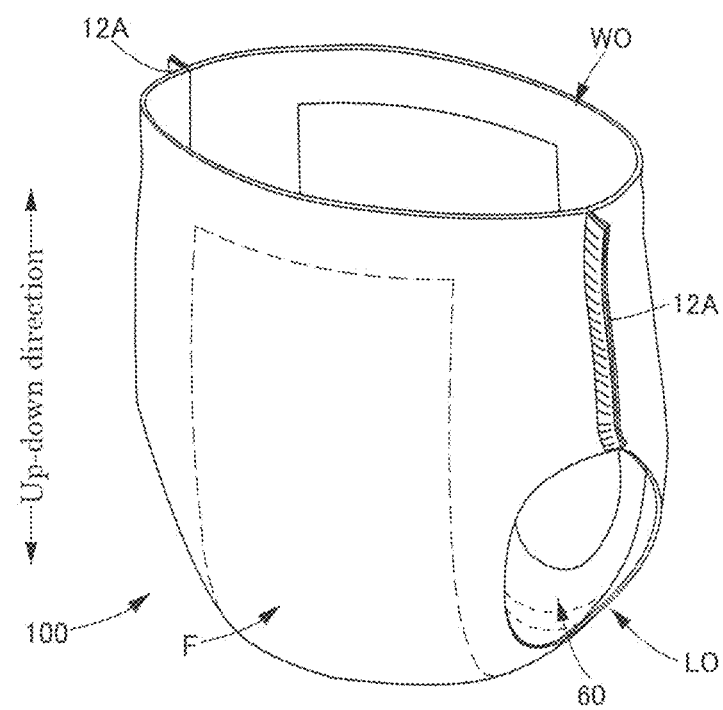
FIG. 8 is a perspective view of the underpants-type disposable diaper.

The outer body 12 has a part constituting a front panel F extended from the crotch portion to the ventral side and a part constituting a back panel B extended from the crotch portion to the dorsal side. The front panel F and the back panel B are joined together at the both sides to form a waist opening WO through which the wearer's waist is passed and a pair of right and left leg openings LO through which the wearer's legs are passed as illustrated in FIG. 8. Reference sign 12A indicates joined section (hereinafter, also referred to as side seal portions). The crotch portion refers to a central portion in the front-back direction from the waist edge of the front panel F to the waist edge of the back panel B in an open state. The portions on the front side and the back side of the crotch portion refer to the front panel F and the back panel B, respectively.

The outer body 12 has waist portion T determined as front-back areas from the waist opening WO to the upper ends of the leg openings LO, and an intermediate portion L determined as a front-back area forming the leg openings LO (between the front-back area having the side seal portions 12A of the front panel F and the front-back area having the side seal portions 12A of the back panel B). The waist portion T is conceptually divided into waist edge portion W forming the edge of the waist opening and lower waist portion U as the portion under the waist edge portion W. Usually, when the waist portion T has a boundary where stretch stress in the width direction changes (the thickness or the extension ratio of the resilient and elastic members changes, for example), the side which is closer to the waist opening WO than the boundary closest to the waist opening WO is the waist edge portion W. When the waist portion T does not have such a boundary, the side closer to the waist opening WO than the absorber 56 or the inner body 200 is the waist edge portion W. The lengths of these portions in the vertical direction vary depending on the size of the product and can be decided as appropriate. As an example, the length of the waist edge portion W may be 15 to 40 mm, and the length of the lower waist portion U may be 65 to 120 mm. The both side edges of the intermediate portion L are narrowed so as to fit around the wearer's legs, and the wearer's legs are placed through this region. As a result, the outer body 12 has an almost hourglass shape as a whole. The degree of narrowing of the outer body 12 can be decided as appropriate. As in the forms illustrated in FIGS. 1 to 8, the outer body 12 is preferably narrower than the inner body 200 at the narrowest area in width for simple appearance. Alternatively, the outer body 12 may be wider than the inner body 200 even at the narrowest area in width.

As illustrated in FIG. 3 to FIG. 6, the outer body 12 is formed by joining two sheet materials 12S and 12H. A first sheet material 12S positioned outside is folded back inside at the edge of the waist opening WO, and the folded part 12r is extended to cover the upper end portion of the inner body 200 at the waist side. In the form illustrated in FIG. 5, the structure is such that a second sheet material 12H positioned inside extends to the end portion of the waist opening WO side in the front panel F, but the second sheet material 12H only extends to the lower position (front-back center side) than a front edge of the second sheet material 12H of the front panel F, in the back panel B. The layer structure of the front panel F can be matched to the layer structure of the back panel B or vice versa.

There is no specific limitation on the sheet materials 12S and 12H as far as they are sheet-like, but they are preferably formed from non-woven fabric. There is no specific limitation on raw fibers for the non-woven fabric. For example, the raw fibers may be synthetic fibers based on olefin such as polyethylene and polypropylene, polyester, or polyamide, reproduced fibers of rayon or cupra, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example.

To enhance the fit around the wearer's waist, in the outer body 12, elongated resilient and elastic members 19 (waist edge portion resilient and elastic members 17, lower waist portion resilient and elastic members 15, intermediate portion resilient and elastic members 16 described later) such as rubber threads are provided at a predetermined extension ratio between the inner layer 21 and the outer layer 22 formed by at least one of both sheet materials 12S and 12H. As the elongated resilient and elastic members 19, synthetic rubber or natural rubber may be used. In the form illustrated in FIG. 5, the waist edge portion of the front panel F of the outer body 12 has the outer layer 22 formed by the first sheet material 12S and the inner layer 21 formed by the second sheet material 12H, as illustrated in FIG. 6(*d*). The waist edge portion of the back panel B of the outer body 12 has the outer layer 22 formed by a portion of the first sheet material 12S positioned on the outer surface side of the diaper and the inner layer 21 formed by portion of the first sheet material 12S that is folded back inside, as illustrated in FIG. 6(*e*). Then, in any part other than this, the outer body 12 has the outer layer 22 formed by the first sheet material 12S and the inner layer 21 formed by the second sheet material 12H.

More specifically, between the inner layer 21 and the outer layer 22 at the waist edge portion W, a plurality of waist edge portion resilient and elastic members 17 is fixed in the extended state along the width direction at a predetermined extension ratio with spacing therebetween in the up-down direction in such a manner as to be entirely continuous in the width direction. One or more of the waist edge portion resilient and elastic members 17 in the area adjacent to the lower waist portions U may overlap the inner body 200 or may be provided at the both sides of the middle portion overlapping the inner body 200 in the width direction. As the waist edge portion resilient and elastic members 17, about 3 to 22 rubber threads with a thickness of 155 to 1880 dtex, in particular about 470 to 1240 dtex (This is applied in the case of a synthetic rubber. In the case of a natural rubber, a cross-section area of 0.05 to 1.5 mm², in particular about 0.1 to 1.0 mm²) are preferably fixed at an extension ratio of 150 to 400%, in particular about 220 to 320%, with spacing of 4 to 12 mm. All of the waist edge portion resilient and elastic members 17 may not be equal in thickness and extension ratio. For example, the resilient and elastic members may be different in thickness and extension ratio between the upper and lower sides of the waist edge portions W.

Between the inner layer 21 and the outer layer 22 in the lower waist portion U of the front panel F and the back panel B, a plurality of lower waist portion resilient and elastic members 15 composed of elongated resilient and elastic members is fixed in the extended state in the width direction at a predetermined extension ratio with spacing therebetween in the up-down direction in such a manner as to be entirely continuous in the width direction, at the upper side and both sides of the lower waist portion U except for central portions in the width direction overlapped with the inner body 200.

As the lower waist portion resilient and elastic members 15 and 18, about 5 to 30 rubber threads with a fineness of 155 to 1880 dtex, in particular about 470 to 1240 dtex (This is applied in the case of a synthetic rubber. In the case of a natural rubber, a cross-section area of 0.05 to 1.5 $mm^2$, in particular about 0.1 to 1.0 $mm^2$) are preferably fixed at an extension ratio of 200 to 350%, in particular about 240 to 300%, with spacing of 1 to 15 mm, in particular 3 to 8 mm.

Between the inner layer 21 and the outer layer 22 in the intermediate portion L of the front panel F and the back panel B, a plurality of intermediate portion resilient and elastic members 16 composed of elongated resilient and elastic members is fixed in the extended state along the width direction at a predetermined extension ratio with spacing therebetween in the up-down direction in such a manner as to be entirely continuous in the width direction, at the both sides of the lower waist portion U except for a central portion in the width direction overlapped with the inner body 200.

As the intermediate portion resilient and elastic members 16, about 2 to 10 rubber threads with a thickness of 155 to 1880 dtex, in particular about 470 to 1240 dtex (This is applied in the case of a synthetic rubber. In the case of a natural rubber, a cross-section area of 0.05 to 1.5 $mm^2$, in particular about 0.1 to 1.0 $mm^2$) are preferably fixed at an extension ratio of 150 to 300%, in particular about 180 to 260%, with spacing of 5 to 40 mm, in particular 5 to 20 mm.

When the lower waist portion resilient and elastic members 15 and the intermediate portion resilient and elastic members 16 are provided at the both sides of the central portions overlapping the inner body 200 in the width direction (including both of an area with same width as the inner body 200 and an area which is a part thereof) except for the central portions as illustrated in the drawings, the inner body 200 does not contract more than necessary in the width direction, thus the diaper does not become rough with deterioration in appearance and does not decrease in absorbing performance. The foregoing form includes the form in which the resilient and elastic members reside only at the both sides in the width direction, and the form in which the resilient and elastic members reside crossing over the inner body 200 from one side to the other side in the width direction, but the resilient and elastic members are finely cut and exert no contraction force at the central portions overlapping the inner body 200 in the width direction (this substantially means that no resilient and elastic members are provided), and thus the contraction force of the resilient and elastic members acts only at the both sides in the width direction. As a matter of course, the arrangement forms of the lower waist portion resilient and elastic members 15 and the intermediate portion resilient and elastic members 16 are not limited to the foregoing examples. Alternatively, some or all of the lower waist portion resilient and elastic members 15 and the intermediate portion resilient and elastic members 16 may be provided crossing over the inner body 200 from the one side to the other side in the width direction so that the stretching force acts on the entire lower waist portions U in the width direction.

(Example of Other Structures of the Outer Body)

Figure 11:
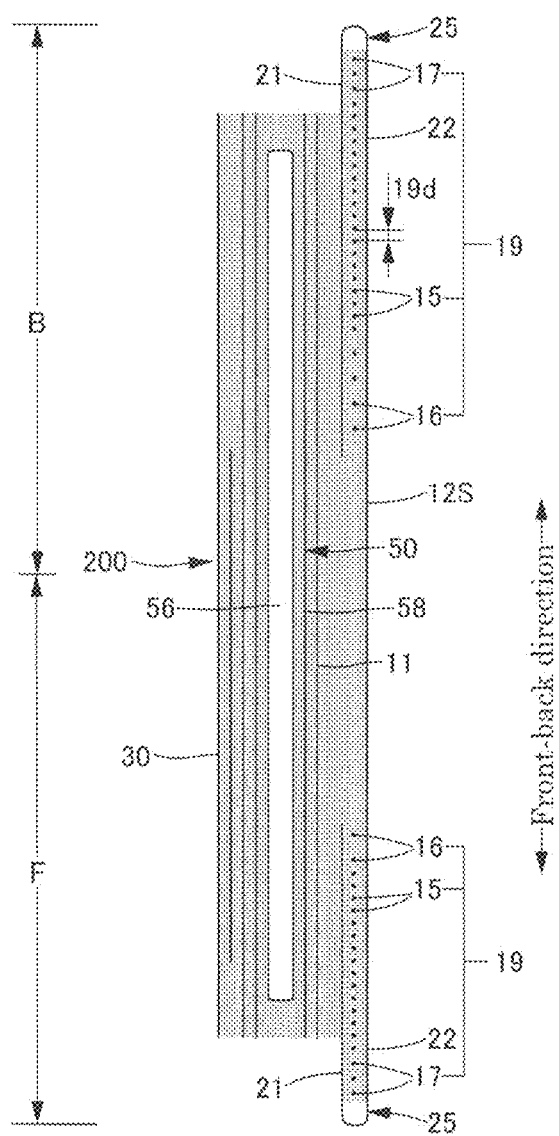
FIG. 11 is a cross-sectional view corresponding to the cross section taken along line 5-5.

As illustrated in FIG. 11, the entire outer body 12 can be formed by folding back both front and back sides of one sheet material 12S.

In addition, in the foregoing example, the integrated outer body 12 covers continuously from the front panel F to the back panel B. Alternatively, the ventral side outer body and the dorsal side outer body may be discontinued and separated from each other at the crotch side (not illustrated). In that case, a crotch portion outer body may be stuck to the outer surface of the inner body 200 to cover the portion exposed between the ventral side outer body and the dorsal side outer body. For the crotch portion outer body, the same material as that for the foregoing outer body can be used. If the outer body is divided to the ventral side and the dorsal side, the inner layer and the outer layer of each outer body may be formed by the first sheet material and the second sheet material similar to the form illustrated in FIG. 5. Alternatively, they may be formed by folding back one sheet material in two or so-called C at the waist opening side.

(Stretchable Structure)

In this underpants-type disposable diaper, a stretchable structure based on the vertical continuous joined form is used in an area from the waist edge portion W to the intermediate portion L. More specifically, as illustrated in FIG. 6, in the area, the inner layer 21 and the outer layer 22 formed by the first sheet material 12S and the second sheet material 12H being intermittently arranged in the width direction, sheet joined sections 70 are formed by being joined with adhesive 71 (hot-melt adhesive or the like) continuing at predetermined width in a direction crossing the width direction (orthogonal in the illustrated form). It is preferable that width direction dimension 70w of each sheet joined section 70 is 0.5 to 4 mm and that spacing 70d between adjacent sheet joined sections 70 is 4 to 8 mm (preferably 5 to 7 mm). A lower limit of the width direction dimension 70w of the sheet joined section 70 is preferably 1 mm from the viewpoint of easiness of producing, but is preferably 0.5 mm from the viewpoint of flexibility. Meanwhile, an upper limit of the width direction dimension 70w of the sheet joined section 70 is preferably 2 mm and more preferably 1.5 mm.

There is no particular limitation on the material for the first sheet material 12S and the second sheet material 12H, but each of them is desirably non-woven fabric having thickness of 0.1 to 1 mm and basis weight of 10 to 20 $g/m^2$. Note that each of the first sheet material 12S and the second sheet material 12H may be composed of one piece of non-woven fabric or alternatively, and any one or both of the first sheet material 12S and the second sheet material 12H may be a laminated body of more than one piece of non-woven fabric.

Flexible non-woven fabric is preferable. For at least one of the first sheet material 12S and the second sheet material 12H, non-woven fabric of polypropylene (PP) or copolymer thereof (for example, copolymer having polyethylene or ethylene blended as a copolymer component) (hereinafter referred to as PP non-woven fabric) or non-woven fabric of core-sheath fiber (PE/PP) having polyethylene (PE) as a sheath and polypropylene (PP) as a core, or the like is suitable. In addition, there is no particular limitation on a non-woven fabric type, but spun-bonded non-woven fabric is preferable as it has excellent strength and flexibility. In particular, spun-bonded non-woven fabric formed by laminating a plurality of spun-bonded layers such as SS non-woven fabric (two layers) or SSS non-woven fabric (three layers) can be suitably used. Spun-bonded non-woven fabric of four or more layers can also be used.

The resilient and elastic members 15 to 17 are fixed by the adhesive 71 to at least one of the inner layer 21 and the outer layer 22 at positions intersecting with the sheet joined sections 70. To fix the resilient and elastic members 15 to 17, a different adhesive from that for forming sheet joined sections can be applied to the resilient and elastic members or the inner layer 21 and the outer layer 22. In the illustrated form, however, since the adhesive 71 for forming sheet joined sections 70 is continuous in the direction crossing the width direction, the adhesive 71 is used to fix the resilient and elastic members 15 to 17 to at least one of the inner layer 21 and the outer layer 22. During producing, the adhesive 71 may be applied to any one or both of the inner layer 21 and the outer layer 22, and the resilient and elastic members 15 to 17 may be sandwiched between the inner layer 21 and the outer layer 22 when the inner layer 21 and the outer layer 22 are joined.

In the form illustrated in FIG. 6, the adhesive 71 is applied to the inner surface of the outer layer 22 intermittently in the width direction and continuously at predetermined width in the direction crossing the width direction. No adhesive 71 is applied to the outer surface of the inner layer 21, and the resilient and elastic members 15 to 17 are sandwiched in the extended state between the inner layer 21 and the outer layer 22. Then, the inner layer 21 and the outer layer 22, and the resilient and elastic members 15 to 17 are respectively bonded by the adhesive 71. In this case, since the adhesive 71 is continuous in the direction crossing the width direction outside the resilient and elastic members 15 to 17 in the parts where the sheet joined sections 70 intersect with the resilient and elastic members 15 to 17, the resilient and elastic members 15 to 17 are fixed to the outer layer 22, and the adhesive 71 is discontinued in the direction crossing the width direction inside the resilient and elastic members 15 to 17. In the figure, reference sign 72 indicates the discontinued part. Intermittent presence of the adhesive 71 in the inner layer 21 enables control of reduction in flexibility of the inner layer 21 and thus, reduction in flexibility of the outer body 12 as a whole. In addition, in the resilient and elastic members 15 to 17, the adhesive 71 is continuous only on the outside at the positions intersecting with the sheet joined sections 70. Nevertheless, since the inner layer 21 and the outer layer 22 are integrated by the sheet joined sections 70 at both sides of the resilient and elastic members 15 to 17 in the vertical direction, the contraction force of the resilient and elastic members 15 to 17 acts on the inner layer 21 and the outer layer 22 almost equally, and equal wrinkles can thus be formed on both of the inner layer 21 and the outer layer 22.

It is also possible to apply the adhesive 71 to both of the inner layer 21 and the outer layer 22 in a similar pattern. In this case, as illustrated in FIG. 12, there is an advantage that the resilient and elastic members 15 to 17 can be fixed more firmly because the adhesive is continuous at predetermined width in the direction crossing the width direction at both inside and outside the resilient and elastic members 15 to 17 in the parts where the sheet joined sections 70 intersect with the resilient and elastic members 15 to 17. As in the example illustrated in FIG. 11, in particular, if the inner layer 21 and the outer layer 22 are formed by a portion positioned inside the one sheet material 12S which is folded back at the waist opening WO and by a portion positioned outside the one sheet material 12S, the diaper can be produced simply by folding the sheet material 12S in two or so-called C in the middle of a direction in which the adhesive 71 continues, after applying the adhesive 71 on the one sheet material 12S in a vertically striped pattern. Hence, there is an advantage that a position gap between the adhesive 71 on the inner layer 21 side and the adhesive 71 on the outer layer 22 side can be prevented. As a matter of course, when the inner layer 21 and the outer layer 22 are formed of one sheet material 12S, material cost can be reduced. In addition, although not illustrated, it is also possible to apply the adhesive 71 to the inner layer 21, and sandwich and fix the resilient and elastic members without applying the adhesive 71 to the outer layer 22. However, these forms are less preferable because the adhesive 71 is continuous in the inner layer 21, which reduces flexibility of the second sheet material 12H itself that is in contact with skin, and a part with the reduced flexibility is pressed against skin by the resilient and elastic members 15 to 17.

A hot-melt adhesive is suitably used for the adhesive 71 for forming the sheet joined sections 70. Hot-melt adhesives including EVA-based, adhesive rubber-based (elastomer-based), olefin-based, and polyester/polyamide based hot-melt adhesives exist and can be used without any limitation, but use of the adhesive-rubber based (elastomer-based) hot-melt adhesive is preferred.

Figure 19:
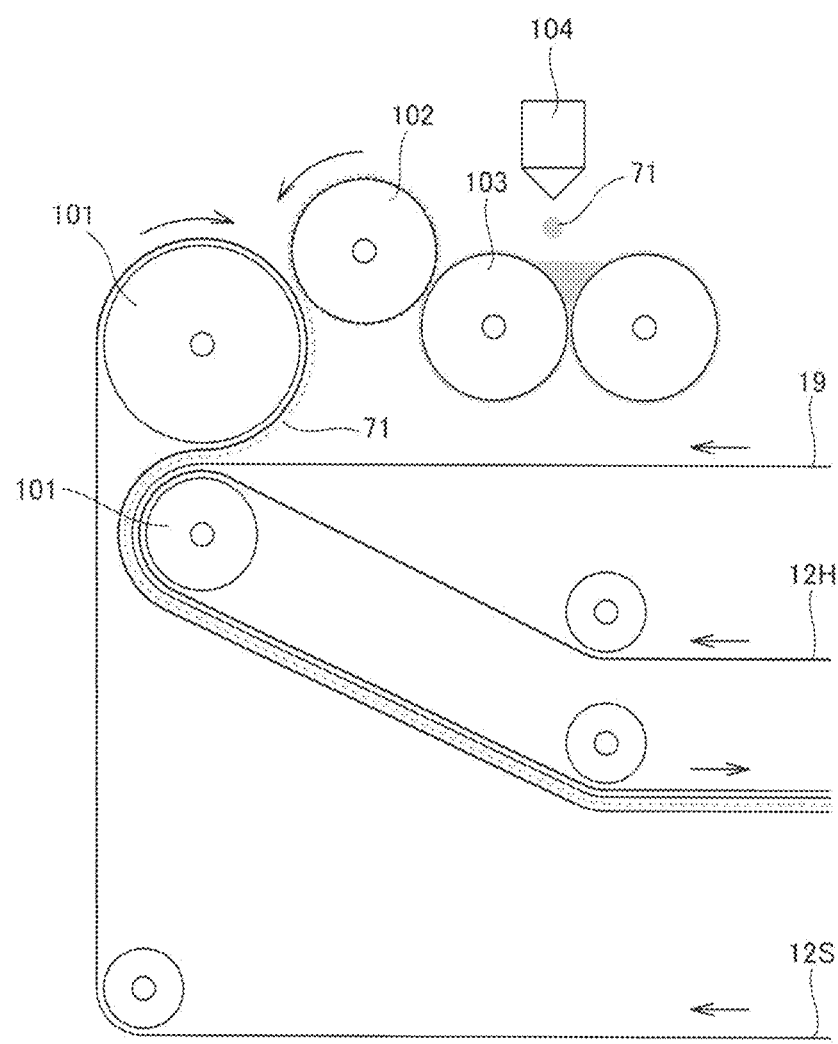
FIG. 19 is a schematic view of bonding equipment.
Figure 20:
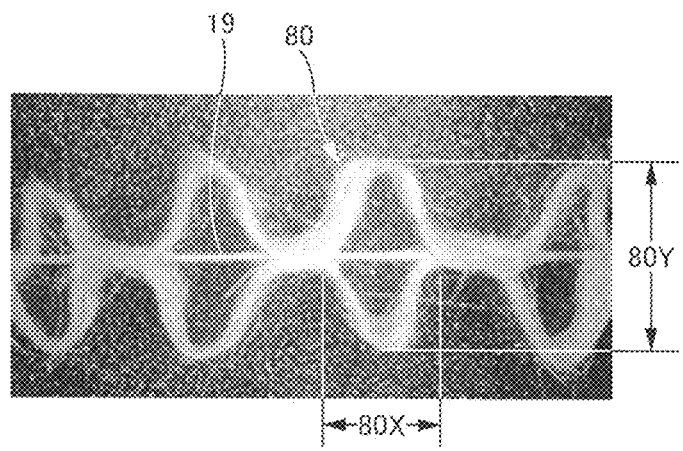
FIG. 20 are microscope photographs.
Figure 20:
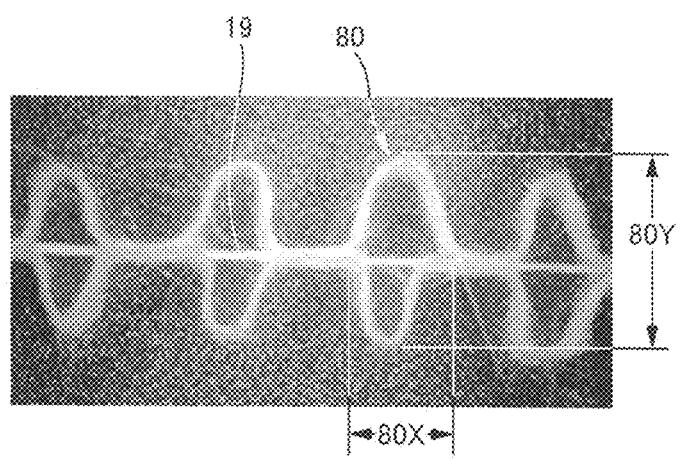

There is no particular limitation on a method of applying a hot-melt adhesive. However, when the width direction dimension of the sheet joined section 70 is small, for example 1 mm or less, application width of the hot-melt adhesive is narrow. Since application is difficult with intermittent application by a nozzle injection application method such as curtain or solid coating or the like, it is preferable to adopt pattern coating (transfer of the hot-melt adhesive 71 with the relief printing method) suitable for application to thin width. FIG. 19 illustrates an example of producing equipment of a stretchable structure when pattern coating of a hot-melt adhesive is used. More specifically, in this equipment example of the pattern coating method, the resilient and elastic members 15 to 17 are sandwiched between the second sheet material 12H and the first sheet material 12S to a second sheet material 12H side surface of which the hot-melt adhesive 71 is applied, and fed to a pair of nip rolls 101, and pressed and attached, thereby forming the stretchable structure illustrated in FIG. 6. Before being fed to the nip roll 101, the first sheet material 12S is brought into contact with a plate roll 102 having intermittent convex patterns in a circumferential direction, and the adhesive 71 is transferred and applied intermittently in a carrying direction (MD direction. The direction is a width direction), and continuously in a direction (CD direction) crossing the carrying direction. Reference sign 103 indicates a hot-melt adhesive supply roll (anilox roll in the relief printing) for transferring and applying the hot-melt adhesive 71 at predetermined thickness to convex patterns of the plate roll 102, and reference sign 104 indicates a supply nozzle that supplies the hot-melt adhesive 71 to the hot-melt adhesive supply roll 103.

Even when the coating method with such pattern coating is adopted, the hot-melt adhesive 71 may show stringiness depending on a type of the hot-melt adhesive 71, resulting in the risk of less precision of the application width (more specifically, the width of the sheet joined section 70) or decreased operation stability. Thus, it is preferable to use the hot-melt adhesive 71 that has melt viscosity of 10000 mpas or less at temperature of 140° C., the melt viscosity of 5000 mpas or less at temperature of 160° C., and loop tack adhesion of 2000 g/25 mm or more. This reduces the risk of stringiness, and can improve precision of the application width and operation stability.

In addition, the loop tack adhesion of the hot-melt adhesive 71 signifies a value measured as follows. Specifically, a hot-melt adhesive 71 is applied to a 50 μm-thick PET plate in thickness of 50 μm. Then, the plate is cut into a tape having size of 25 mm wide and 125 mm long, and a loop is made by overlapping both ends of the tape. After being fixed to the LT-100 type loop tack tester (manufactured by Chem-instruments, Inc.), the loop is bonded to the PE (polyethylene) plate for a bonding area of 25 mm×25 mm and with binding time of 2 seconds. Then, at 20° C., the loop-shaped tape is torn off at a tearing off speed of 300 mm/minute at 20° C. Then, maximum force is measured and defined as the loop tack adhesion.

In addition, the melt viscosity of the hot-melt adhesive 71 is measured at prescribed temperatures, using a Brookfield type B viscometer (spindle No. 027) according to JIS Z 8803.

Figure 14:
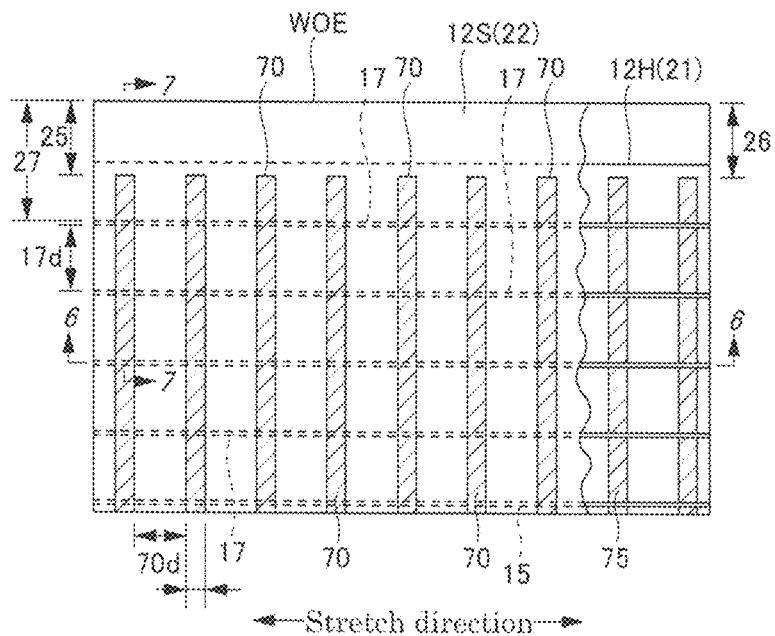
FIGS. 14(a) to (d) illustrate stretchable structures.
Figure 14:
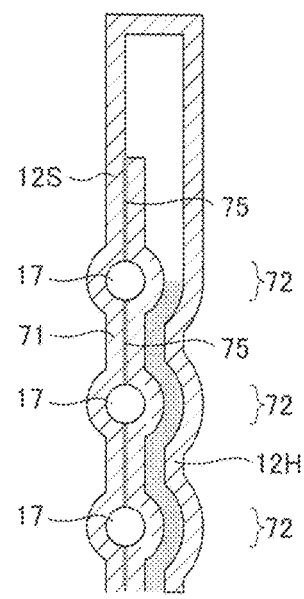
Figure 14:
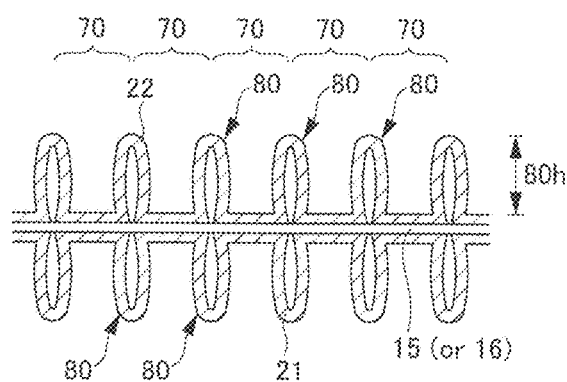
Figure 14:
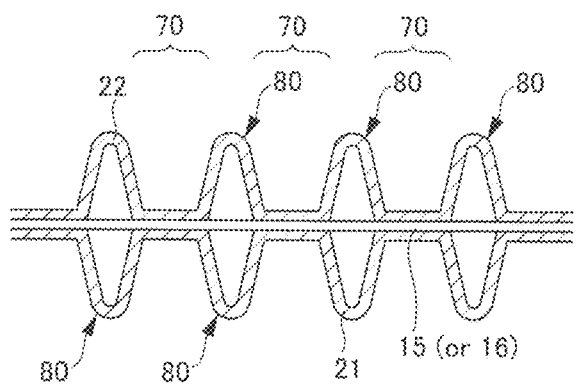

As illustrated in FIG. 14, the sheet joined sections 70 can also be formed by a welding process. Reference sign 75 indicates a welded portion. Any publicly known processing method such as a heat seal, ultrasonic welding, or the like can be used. A continuous welding process for forming the sheet joined sections 70 mentioned herein includes not only a form in which as far as a trace of the welding process continues on at least one of the inner layer 21 and the outer layer 22, the inner layer 21 and the outer layer 22, and the resilient and elastic members 15 to 17 are respectively welded and welding continues as the inner layer 21 and the outer layer 22 are indirectly welded, but also a form in which welding between the inner layer 21 and the outer layer 22 does not continue because the resilient and elastic members 15 to 17 intervene in the parts 72 where the sheet joined sections 70 intersect with the resilient and elastic members 15 to 17. For example, with the resilient and elastic members 15 to 17 sandwiched between the inner layer 21 and the outer layer 22, if welding is performed in a continuous pattern across the resilient and elastic members 15 to 17 by a heat seal or ultrasonic welding, and the inner layer 21 and the outer layer 22 are melted without melting the resilient and elastic members 15 to 17, the stretchable structure takes the latter one, because the inner layer 21 and the outer layer 22 and the resilient and elastic members 15 to 17 are not welded.

Figure 15A:
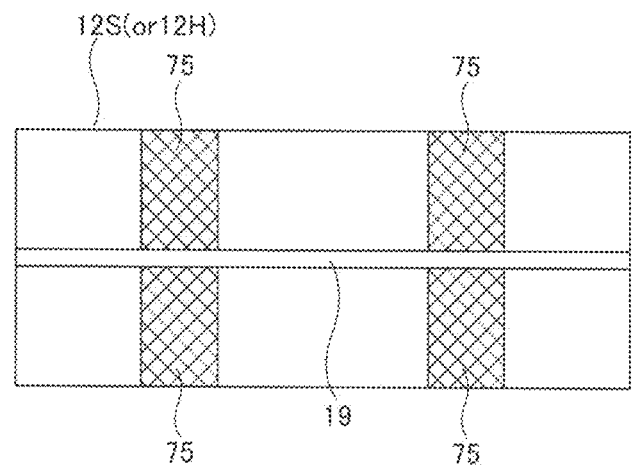
FIG. 15(a) is a planar view illustrating a main part in an extended state and FIG. 15(b) is a planar view illustrating the main part in a contracted state.
Figure 15B:
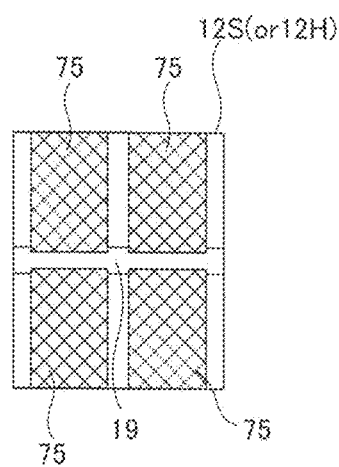

The resilient and elastic members 15 to 17 are fixed to at least one of the inner layer 21 and the outer layer 22 at positions intersecting with the sheet joined sections 70. This fixing form includes not only a form in which the resilient and elastic members 15 to 17 and the sheet are bonded (this includes welding in addition to bonding by the adhesive 71 such as a hot-melt adhesive) at the positions where the resilient and elastic members 15 to 17 intersect with the sheet joined sections 70, but also a form in which although the resilient and elastic members 15 to 17 and the sheet are not bonded, spacing of the sheet joined sections 70 in the direction crossing the width direction is narrower than thickness of the each resilient and elastic member 15 to 17 when it is of natural length, and as a result of the resilient and elastic members 15 to 17 being sandwiched between the sheet joined sections 70 and thus fixed, the contraction force of the resilient and elastic members 15 to 17 is transferred to the sheet at the positions intersecting with the sheet joined sections 70 (refer to JP-A No. 2008-154998 and JP-A No. 2009-106667). More specifically, in the latter form, the stretchable structure can be produced as follows: with the resilient and elastic members 19 stretched to an extension ratio higher than that at the time of fixing inserted between the inner layer 21 and the outer layer 22, as illustrated in FIG. 15(*a*), the sheet joined sections 70 are welded in a continuous pattern across the resilient and elastic members 19 by a heat seal or ultrasonic welding, and the inner layer 21 and the outer layer 22 are melted without melting the resilient and elastic members 19. Without welding the inner layer 21 and the outer layer 22 with the resilient and elastic members 19, tension of the resilient and elastic members 19 is subsequently released, as illustrated in FIG. 15 (*b*), to contract the resilient and elastic members 19 to expand its diameter, thus having the resilient and elastic members 19 sandwiched between the sheet joined sections 70. With this, the stretchable structure to be produced is in the form in which although a trace of welding process is continuous on at least one of the first sheet material 12S and the second sheet material 12H, welding between the inner layer 21 and the outer layer 22 is not continuous as the resilient and elastic members 19 intervene at the parts where the sheet joined sections 70 intersect with the resilient and elastic members 19, and the resilient and elastic members 19 are sandwiched between the sheet joined sections 70.

When the sheet joined sections 70 are formed by welding, hardening of welded portions 75 is inevitable. However, the effect of hardening is less if the dimension of the sheet joined section 70 falls within the range described above. In addition, as a second-order effect, transparency of the welded portions 75 increases and glossy welded portions 75 can achieve stripe-patterned appearance.

Spacing 19*d* between the adjacent resilient and elastic members 19 can be defined appropriately. When the spacing of the adjacent resilient and elastic members 19 exceeds 10 mm, however, thickness of the pleats 80 changes to the direction crossing the width direction, and the pleats 80 become rough, although the change is not as much as the vertical intermittent joined form. Therefore, in the present invention, the spacing 19*d* between the adjacent resilient and elastic members 19 is preferably 10 mm or less, and 3 to 7 mm, in particular.

The thickness and the extension ratio (extension ratio when the stretchable structure is completely unfolded) of the resilient and elastic members 19 may be appropriately selected depending on mounting positions of the resilient and elastic members 19. A preferred range is as described above. In general, it is desirable that the thickness of the each resilient and elastic member 19 is approximately 300 to 1,000 dtex and the extension ratio is approximately 200 to 350%.

In the stretchable structure described above, as the resilient and elastic members 15 to 17 contract, as illustrated in FIG. 6(*b*), portions of the inner layer 21 and the outer layer 22 positioned between the sheet joined sections 70 swell to an opposite direction to each other, thus forming the pleats 80. FIG. 6(*b*) illustrates a state of natural length. The resilient and elastic members 15 to 17 are extended to some extent when the diaper is worn, and as illustrated in FIG. 6(*c*), a bottom of the pleat 80 widens and height 80*h* of the pleat 80 also decreases, accordingly. In addition, since the stretchable structure is of the vertical continuous joined form, the pleats 80 extending straight along the sheet joined sections 70 are formed, which results in excellent air permeability and appearance.

The width direction dimension 70*w* of each sheet joined section 70 has an effect on the spacing between the adjacent pleats 80. As with the vertical continuous joined form, if the width 70w exceeds 4 mm when the formed pleats 80 are thin, the spacing between the adjacent pleats 80 is too wide, and individual pleats 80 look independent. In addition, when the pleats 80 are deformed by collapsing and widening, lying down, or the like due to compressive force in a thickness direction, the action of the adjacent pleats 80 supporting each other weakens. Consequently, resistance to deformation or restoration after deformation also weakens, resulting in insufficient softness.

Yet, only setting the dimension 70w of the sheet joined section 70 to 0.5 to 4 mm, and setting the spacing 70d between the adjacent sheet sections 70 to less than 4 mm or over 8 mm result in the following: Specifically, the spacing 70d between the adjacent sheet joined sections 70 has an effect on height 80h or width of the pleats 80. When the spacing 70d between the adjacent sheet joined sections 70 is approximately 2 mm, the pleats 80 have poor vertical continuity as with the case in which the pleats 80 are continuously fixed in the width direction (thus it makes no sense to intermittently provide sheet joined sections 70 in the width direction). When the spacing 70d between the adjacent sheet joined sections 70 is 3 mm, the action of adjacent pleats 80 supporting each other is not expected although pleats 80 extend straight to the direction orthogonal to the width direction, and softness is short. In addition, when the spacing 70d between the sheet joined sections 70 exceeds 8 mm, the pleats 80 collapse irregularly due to contraction during packing, resulting in poor product appearance. In contrast, only when the width direction dimension 70w of the sheet joined section 70 is set to 0.5 to 4 mm and the spacing 70d between the sheet joined sections 70 is set to 4 to 8 mm, sufficient softness is achieved and the pleats 80 do not easily collapse irregularly due to contraction during packing. Therefore, even if particularly flexible non-woven fabric is used for at least one of the first sheet material and the second sheet material, the pleats 80 do not easily become thin, not easily lie down, and have rich compression resilience.

Non-woven fabric is suitable as the inner layer 21 and the outer layer 22. In that case, however, if the bending resistance in the width direction is low, pleats 80 not only have thin and sharp shape but also are easy to lie down. In addition, the compression resilience in the thickness direction is poor. It is possible to increase basis weight of non-woven fabric to improve this, but there is the risk that the diaper may be coarse (excessively enhanced rigidity) and lack softness when touched, although it looks fluffy. Then, it is proposed to use non-woven fabric as the inner layer 21 and the outer layer 22 to make bending resistance in the width direction higher than that in the direction orthogonal to the width direction. With this, not only pleats 80 easily swell roundly and the compression resilience in the thickness direction is rich, but also the pleats 80 do not lie down easily and yet have rich softness when touched. The bending resistance in the width direction of the inner layer 21 and the outer layer 22 is preferably 30 to 75 mm, more preferably 40 to 55 mm. The bending resistance in the direction orthogonal to the width direction is less than that in the width direction, preferably 20 to 50 mm, more preferably 25 to 35 mm.

The bending resistance of non-woven fabric mentioned herein means a value measured according to the bending resistance method A (45° cantilever method) in JIS L1096: 2010 "Testing methods for woven and knitted fabrics".

To make the bending resistance in the direction orthogonal to the width direction of non-woven fabric less than the bending resistance in the width direction, the stretchable structure may be configured such that fiber orientation of the non-woven fabric follows the width direction. The fiber orientation mentioned herein is a direction which fibers of non-woven fabric follows, and "fiber orientation follows the width direction" refers to non-woven fabric in which, of the total fiber weight constituting the non-woven fabric, 100% of fibers are oriented to the width direction to non-woven fabric in which 50% or more of fibers are oriented to have the fiber orientation with respect to the width direction in a range of −45° to +45°. A generally used measurement method can be used for a method of measuring the fiber orientation of non-woven fabric. Example of the measurement method includes a measurement method according to the test method for fiber orientation in paper (zero-span tensile strength) of TAPPI Standard test method T481 or a simplified measurement method to determine a fiber orientation direction from a ratio of tensile strength in the width direction to that in the direction orthogonal thereto. In the latter simplified measurement method, a tension test is carried out on a test piece of 200 mm long and 50 mm wide using a tension tester under the conditions of a crosshead speed of 500 mm/min and inter-chuck distance of 150 mm to determine tensile strength from maximum load at the time of tension. When a ratio (width direction/orthogonal direction) of the tensile strength is 1 or higher, it is determined that the fiber orientation follows the width direction.

Since the sheet joined sections 70 are intermittent in the width direction in the stretchable structure of the present invention, it is inevitable that fixing force of the resilient and elastic members 15 to 17 decreases resulting in the risk that the resilient and elastic members 15 to 17 may fall out. In particular, although it is desirable that the width direction dimension 70w of each of the sheet joined sections 70 is narrow, in that case, positions where the resilient and elastic members 15 to 17 intersect with the sheet joined sections 70 become small, which necessitates fixing of the resilient and elastic members 15 to 17 at the small position. Hence, it is important to ensure the fixing force of the resilient and elastic members 15 to 17.

Figure 9:
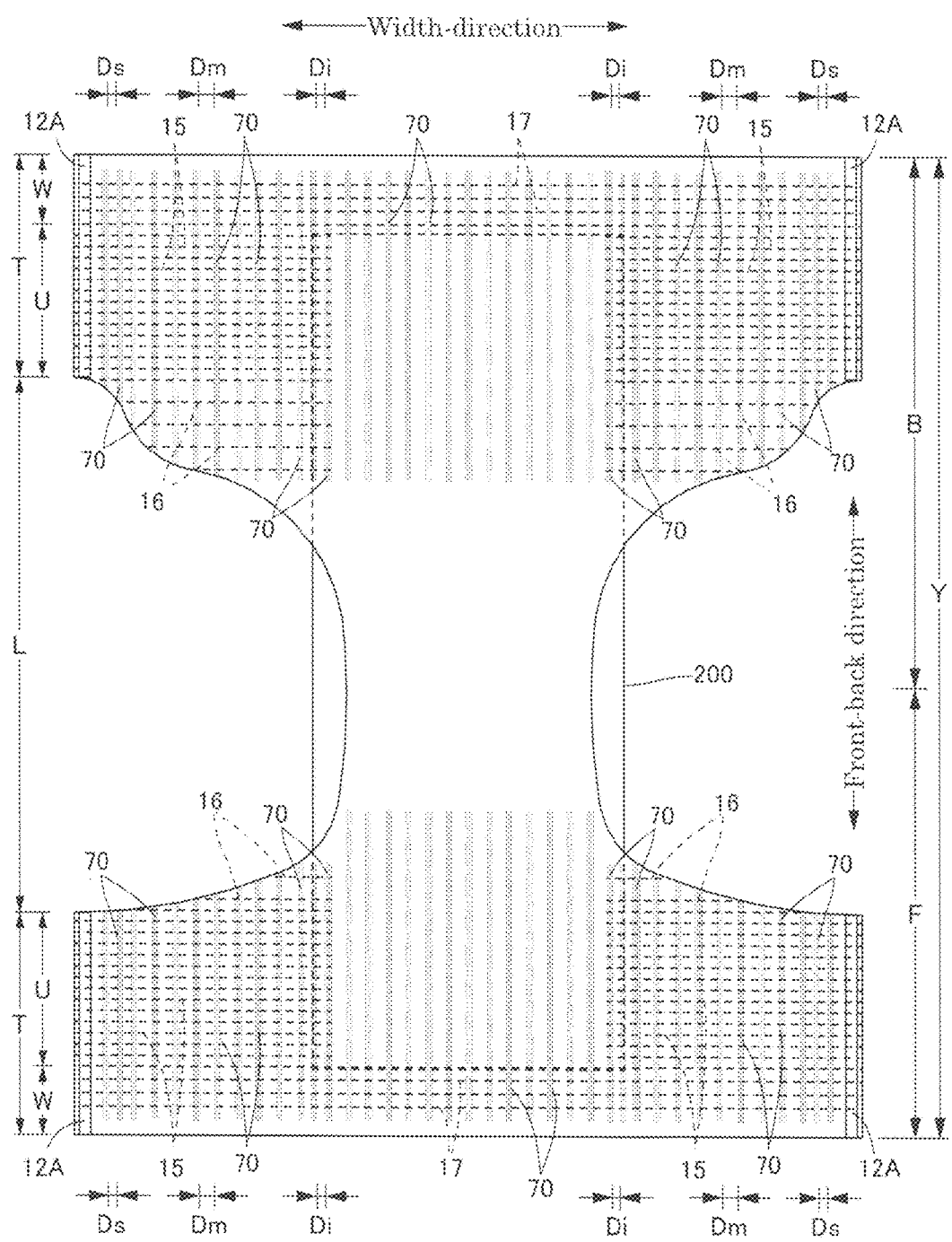
FIG. 9 is a planar view of an outer surface of the underpants-type disposable diaper in the open state.

As a solution to this, as illustrated in FIG. 9, each of the areas in the outer body 12 at both sides of the inner body 200 in the width direction is divided into end portion area on the side of inner body 200, end portion area on the side of side seal portion 12A, and intermediate area positioned therebetween. Then, it is desirable to set each spacing Di, Ds between the sheet joined sections 70 in the end portion area on the side of the inner body 200 and in the end portion area on the side of the side seal portion 12A narrower than spacing Dm between the sheet joined sections 70 in the intermediate area.

Figure 10:
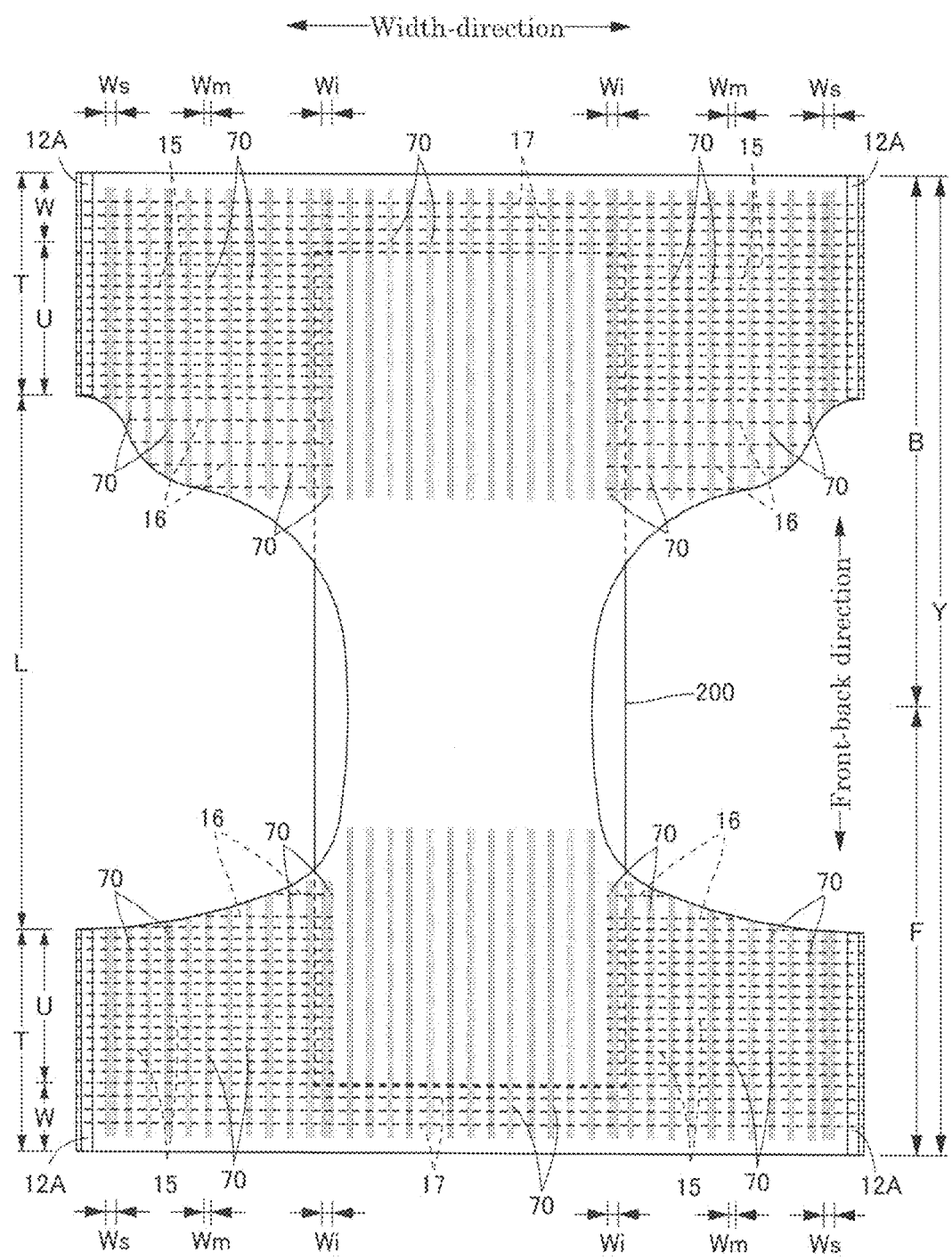
FIG. 10 is a planar view of an outer surface of the underpants-type disposable diaper in the open state.

In addition, instead of the form illustrated in FIG. 9 (it is also possible to combine the form illustrated in FIG. 9), as illustrated in FIG. 10, a form is also preferable in which each fixed width Wi, Ws (equal to the width direction dimension 70w of the sheet joined section 70 in the illustrated form) of the resilient and elastic members 15 to 17 in the end portion area on the side of the inner body 200 and in the end portion area on the side of the side seal portion 12A is set wider than fixed width Wm of the resilient and elastic members in the intermediate area.

In addition, since outer end portions in the width direction of the resilient and elastic members 15 to 17 of the outer body 12 of the underpants-type disposable diaper are firmly fixed in the side seal portions 12A, a form is also preferable that the fixing and strengthening means is omitted in the end portion area on the side seal portion 12A.

<Area not being Joined and not Having Resilient and Elastic Member>

The diaper is characterized in that, as illustrated in FIG. 5, FIG. 6, and FIG. 11 to FIG. 14, the area 25 not being joined and not having resilient and elastic member has no sheet joined section 70 and waist edge portion resilient and elastic members 17 at an end portion of the outer body 12 on the side of a waist opening WO in the waist edge portion W and has its vertical range wider than spacing 17d between the waist edge portion resilient and elastic member 17 positioned closest to the waist opening WO side and the waist edge portion resilient and elastic member 17 adjacent thereto. In the illustrated form, the area 25 not being joined and not having resilient and elastic member is provided on both of the front panel F and the back panel B, but the area 25 may be provided only on any one of them.

Figure 16:
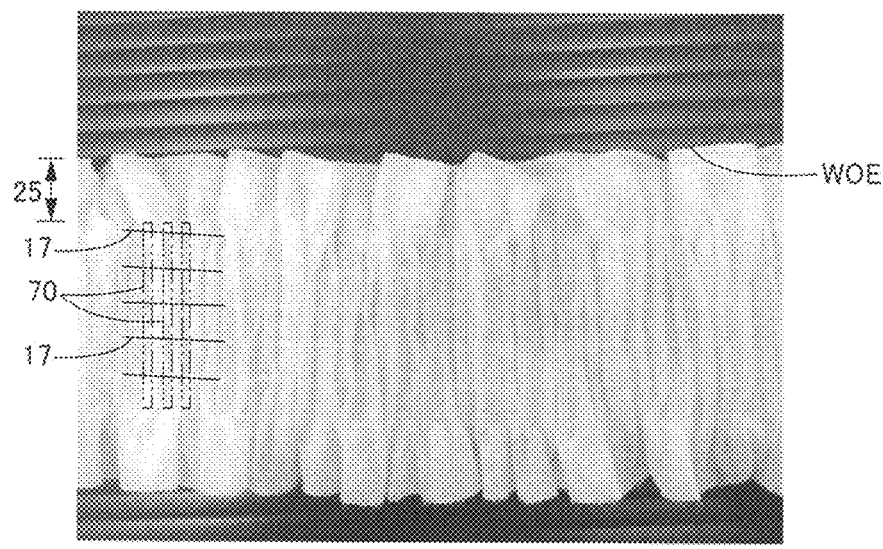
FIGS. 16(a) and (b) are comparison photographs of waist edge portion W samples.
Figure 16:
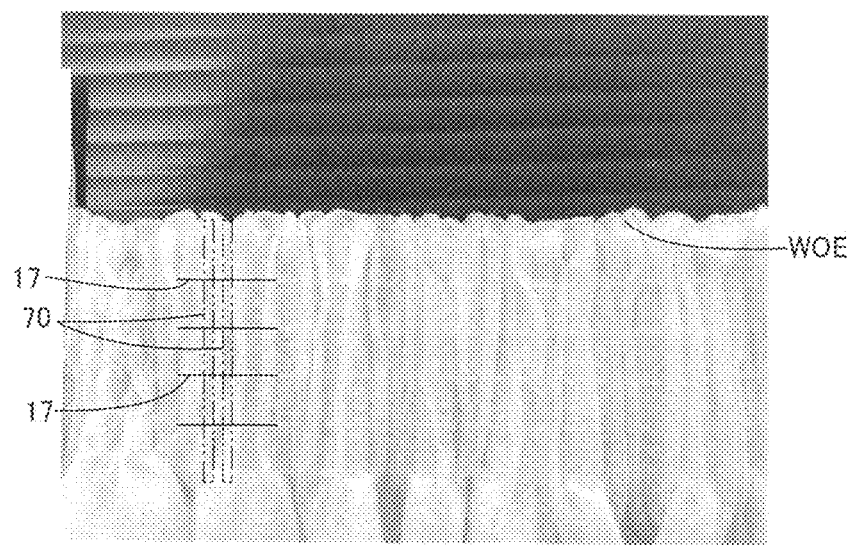
Figure 17:
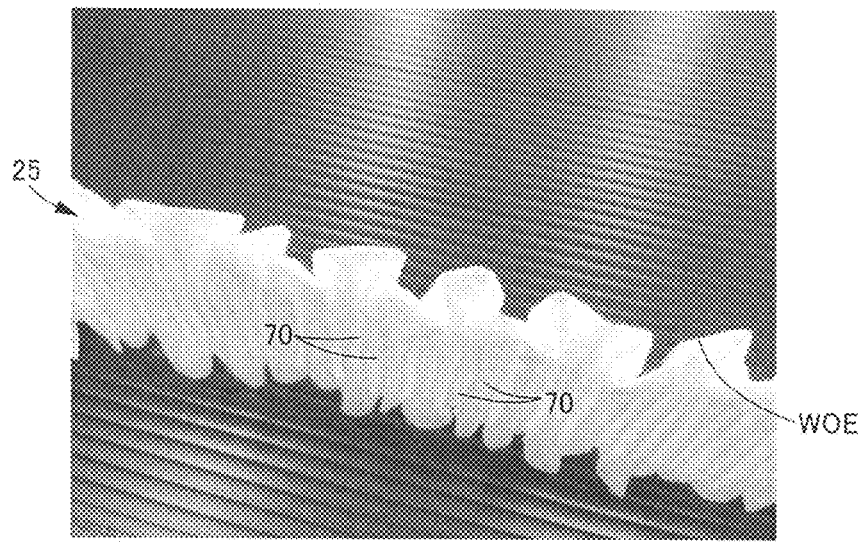
FIGS. 17(a) and (b) are comparison photographs of the waist edge portion W samples.
Figure 17:
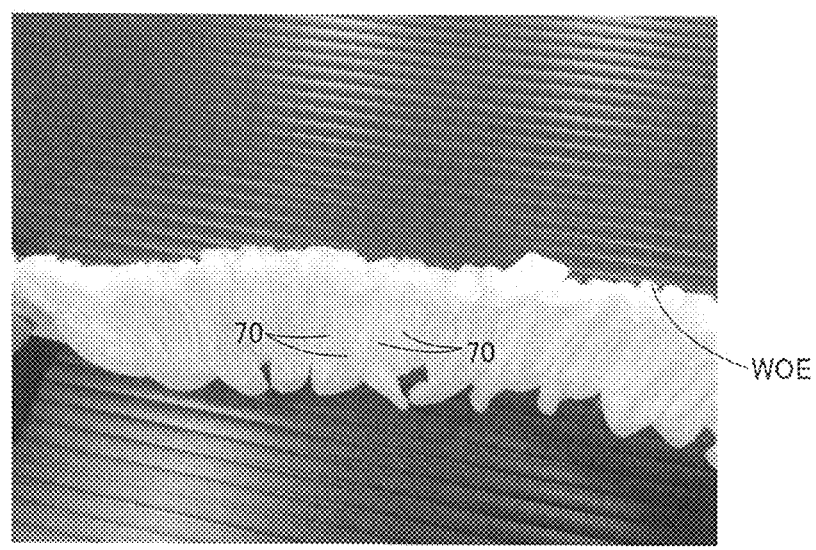

In this manner, if a wide area 25 not being joined and having no resilient and elastic member is ensured in the waist edge portion W while applying the vertical continuous joined form to the waist edge portion W, as can be seen from photographs of part samples of the waist edge portion W shown in FIG. 16(a) and FIG. 17 (a), there is no longer hard sheet joined sections 70 at the end portion on the waist opening W side (area 25 not being joined and not having resilient and elastic member), and contraction wrinkles are larger, sparse, and flexible than in the area having the waist edge portion resilient and elastic members 17. The concavities and convexities at the edge WOE of the waist opening WO are also large, sparse, and flexible, thus achieving good wearing feeling at the waist edge portion W. Yet, since the waist edge portion W of the outer body 12 other than the end portion on the waist opening WO side takes the vertical continuous joined form, contraction wrinkles formed at the waist edge portion W due to contraction of the waist edge portion resilient and elastic members 17 are formed although they are large and sparse at the end portion on the waist opening WO side. Thus, air permeability in the vertical direction due to the contraction wrinkles is hardly reduced. In contrast, if the vertical continuous joined form is applied to the conventional underpants-type disposable diaper, as can be seen from photographs of the part samples of the waist edge portion W shown in FIG. 16(b) and FIG. 17(b), since there is little area 25 not being joined and not having resilient and elastic member in the end portion of the waist edge portion W on the waist opening WO side, hard sheet joined sections 70 vertically continue to the edge of the waist opening WO and fine contraction wrinkles continue tightly in the vertical direction, thus forming highly rigid wavy concavities and convexities at the edge WOE of the waist opening WO and deteriorating wearing feeling at the waist edge portion W.

Figure 6A:
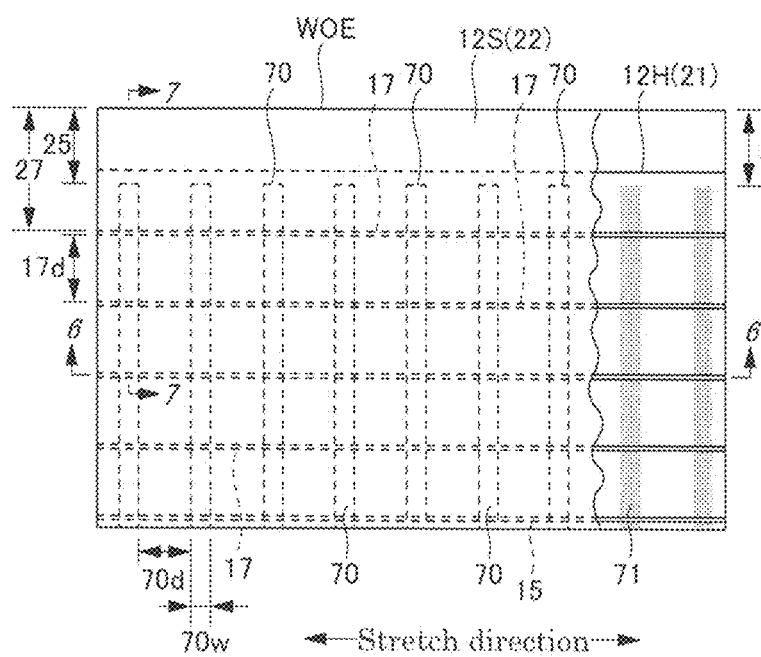
FIGS. 6(a) to 6(e) illustrate stretchable structures.
Figure 6D:
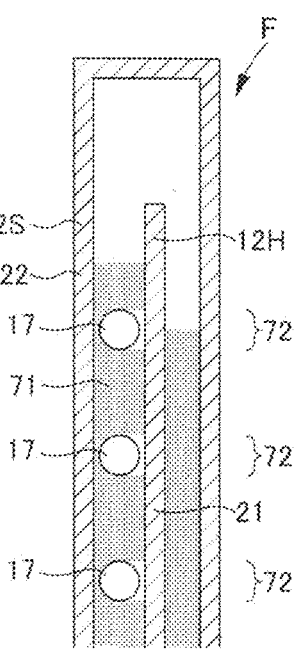
Figure 6B:
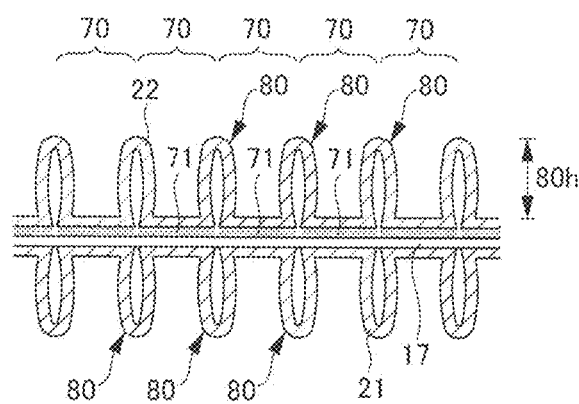
Figure 6E:
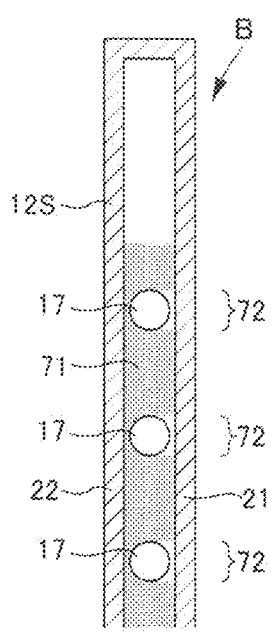
Figure 6C:
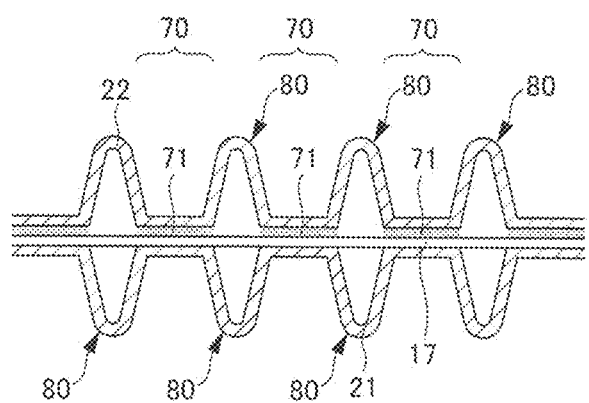

Vertical dimension of the area 25 not being joined and not having resilient and elastic member may be defined appropriately. However, as illustrated in FIG. 6(a), FIG. 12(a), and FIG. 14(a), respectively, it is preferable that distance 26 from the edge WOE of the waist opening WO to a forward end of the sheet joined section 70 on the waist opening WO side is 3 to 15 mm. It is also preferable that the distance 27 from the edge of the waist opening WO to the waist edge portion resilient and elastic member 17 positioned closest to the waist opening WO side is 5 to 20 mm. Since the waist edge portion resilient and elastic members are fixed at the sheet joined sections, the distance 26 from the edge WOE of the waist opening WO to the forward end of the sheet joined section 70 on the waist opening WO side is shorter than the distance 27 from the edge of the waist opening WO to the waist edge portion resilient and elastic member 17 positioned closest to the waist opening WO side. When the distance 26 from the edge of the waist opening WO to the forward end of the sheet joined section 70 on the waist opening WO side is less than 3 mm or when the distance 27 from the edge of the waist opening WO to the waist edge portion resilient and elastic member 17 positioned closest to the waist opening WO side is less than 5 mm, rigidity of the wavy concavities and convexities formed at the edge of the waist opening WO tends to be high. In addition, it is not preferable that the distance 26 from the edge of the waist opening WO to the forward end of the sheet joined section 70 on the waist opening WO side exceeds 15 mm, because then, wrinkles formed in the area 25 not being joined and not having resilient and elastic member tend to be irregular although the improvement effect of wearing feeling at the waist edge portion W remains unchanged. It is also not preferable that the distance 27 from the edge of the waist opening WO to the waist edge portion resilient and elastic member 17 closest to the waist opening WO side exceeds 20 mm, because fit at the waist edge portion degrades.

Figure 13:
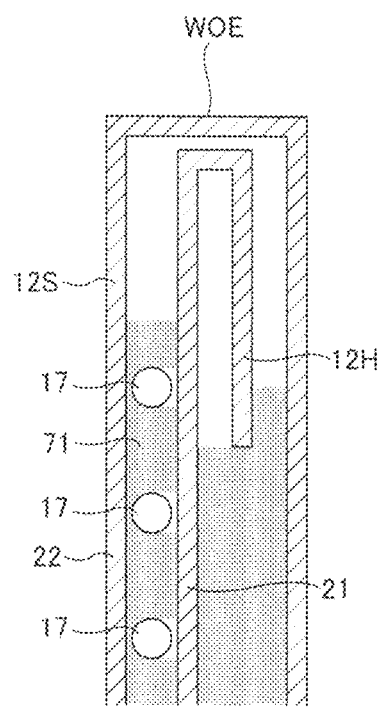
FIGS. 13(a) to (c) are cross-sectional views illustrating various types of stretchable structures.
Figure 13:
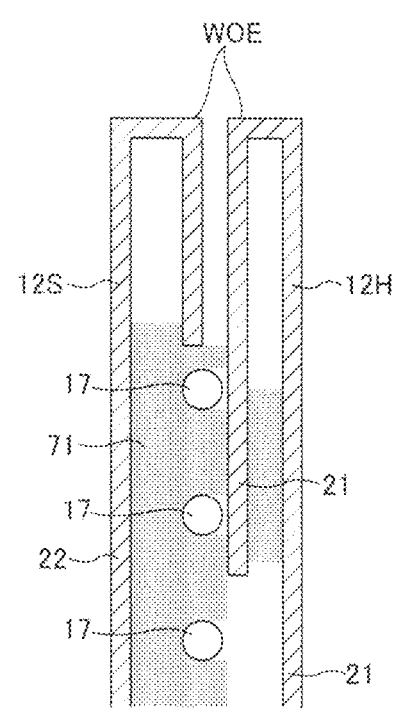
Figure 13:
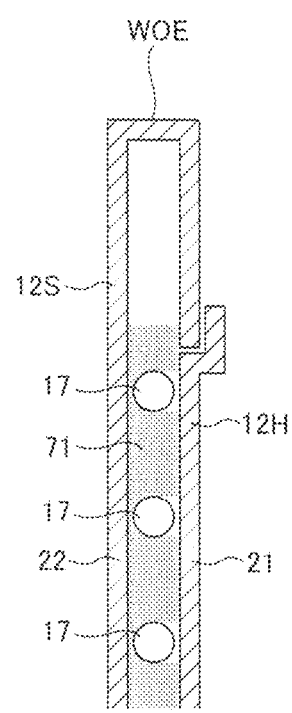

For the number of layers of sheet materials of the area 25 not being joined and not having resilient and elastic member, while it is preferable that the sheet materials have a double-layered structure (only the inner layer 21 and the outer layer 22), as with the back panel B of the form illustrated in FIG. 5 or the form illustrated in FIG. 12, it is preferable that as with the front panel F illustrated in FIG. 5 or the form illustrated in FIG. 13, sheet materials have three or more layered structure by folding back at the waist opening WO at least one of the second sheet material 12H constituting the inner layer 21 and the first sheet material 12S constituting the outer layer 22. In this manner, if the number of the sheet materials in the area 25 not being joined and not having resilient and elastic member is three or more layers, volume of the area 25 not being joined and not having resilient and elastic member increases, and thus it is possible to supplement rigidity without losing flexibility and prevent burr at the edge of the waist opening WO or insufficient formation of contraction wrinkles.

More specifically, in a structure example of the outer body 12 illustrated in FIG. 13(a), the number of layers of the sheet materials in the area 25 not being joined and not having resilient and elastic member is four layers, by integrally folding inside (this may be outside as well) both the second sheet material 12H constituting the inner layer 21 and the first sheet material 12S constituting the outer layer 22 at the edge WOE of the waist opening WO.

In addition, in a structure example of the outer body 12 illustrated in FIG. 13(b), the number of layers of the sheet materials in the area 25 not being joined and not having resilient and elastic member is four layers, by not only folding outside the second sheet material 12H constituting the inner layer 21 at the edge of the waist opening WO and tucking it in spacing with the first sheet material 12S constituting the outer layer 22, but also folding back the first sheet material 12S constituting the outer layer 22 at the edge of the waist opening WO and tucking it in spacing with the second sheet material 12H constituting the inner layer 21. A forward edge of the folded portion of the second sheet material 12H constituting the inner layer 21 and that of the folded part of the sheet material constituting the outer layer may vertically match (be aligned), or may be misaligned as with the illustrated form. In addition, the folded parts may fit in the area 25 not being joined and not having resilient and elastic member or protrude therefrom.

FIG. 13(c) illustrates the form in which the second sheet material 12H constituting the inner layer 21 is extended to the area 25 not being joined and not having resilient and elastic member at the waist edge portion W, and the first sheet material 12S constituting the outer layer 22 is folded inside at the edge of the waist opening WO, so that the folded part overlaps the end portion of the second sheet material 12H constituting the inner layer 21 in the area 25 not being joined and not having resilient and elastic member. Reversely, a configuration, although not illustrated, may be such that the sheet material constituting the outer layer is extended to the area not being joined and not having resilient and elastic member at the waist edge portion and the sheet material constituting the inner layer is folded inside at the edge of the waist opening, so that the folded part overlaps the end portion of the sheet material constituting the outer layer in the area not being joined and not having resilient and elastic member. In addition, at a part where the second sheet material 12H constituting the inner layer 21 overlaps the first sheet material 12S constituting the outer layer 22, either the first sheet material 12S constituting the outer layer 22 or the second sheet material 12H constituting the inner layer 21 may be the inside.

In addition, in the forms illustrated in FIG. 13, the second sheet material 12H constituting the inner layer 21 and the first sheet material 12S constituting the outer layer 22 are designated by different symbols similar to the form illustrated in FIG. 5, but they may be individual sheet materials or one common sheet material.

(Others)

In the above examples, the similar stretchable structures are formed at not only the waist edge portion W but also the lower waist portion U and the intermediate portion L of the underpants-type disposable diaper. However, as far as the waist edge portion W is included, any other publicly known stretchable structure may be applied to the lower waist portion U or the intermediate portion L. Alternatively, the resilient and elastic members 16 in the intermediate portion L may not be provided. In addition, in the above examples, while the sheet joined sections 70 are continuous vertically including the waist edge portion W in each panel, the sheet joined sections 70 in the waist edge portion W and those in the lower waist portion U can be formed individually and with spacing therebetween.

<Experiment 1>

Polypropylene fiber SSS non-woven fabric having fineness of 1.6 denier, basis weight of 17 g/m$^2$, thickness of 0.2 mm (initial thickness T0: thickness under the pressure of 0.5 g/cm$^2$), bending resistance of 55 mm in the MD direction (direction of production line of the non-woven fabric), bending resistance of 28 mm in the CD direction (direction orthogonal to the MD direction) was cut to prepare a first sheet material and a second sheet material having length in the MD direction of 180 m and length in the CD direction of 40 mm. In addition, thread rubber of 470 dtex was prepared as a resilient and elastic member.

A hot-melt adhesive of width of 1 mm being continuous in the CD direction is applied with spacing of 7 mm onto a face of the first sheet material on the second sheet material side in the MD direction. Arranged thereon with spacing of 5 mm in the CD direction were seven rubber threads continuing in the MD direction and each in an extended state of 270%. Then, the second sheet material is arranged thereon aligning the MD direction and the CD direction with that of the first sheet material. The first sheet material, resilient and elastic members, and the second sheet material were placed on the face, and pressed and attached to prepare sample No. 1 of a stretch sheet. Note that natural length of this sample No. 1 in the MD direction was 67 mm. In addition, application width of the hot-melt adhesive was changed to 2 mm, 4 mm, 6 mm, and 10 mm, and application interval of the hot-melt adhesive was changed to 2 mm, 4 mm, 6 mm, 8 mm, and 10 mm, appropriately. Then, samples No. 2 to No. 13 were also prepared.

Formation status of the samples were observed and evaluated on zero-to-four scales. ⊚: Pleats were formed very tidily; ◯: Pleats were formed tidily; Δ: Pleats were formed but not tidily; x: Formation of pleats was not sufficient. The evaluation results were as listed in Table 1. Note that pleats were formed when the application interval of the hot-melt adhesive was 10 mm, but the pleats collapsed during compression because they were too large. The pleats were not formed when the application interval was 2 mm. In addition, when the application width of the hot-melt adhesive was 6 mm and 10 mm, the sheet joined sections also contracted, forming wrinkles.

TABLE 1

|  | No. 1 Example 1 | No. 2 Example 2 | No. 3 Example 3 | No. 4 Example 5 | No. 5 Example 5 | No. 6 Example 6 | No. 7 Comparative Example 1 |
|---|---|---|---|---|---|---|---|
| Hot-melt adhesive application width (mm) | 1 | 2 | 2 | 2 | 4 | 4 | 2 |
| Hot-melt adhesive application interval (mm) | 7 | 4 | 6 | 8 | 4 | 6 | 2 |
| Results of observation of pleat formation status | ⊚ | ◯ | ⊚ | ⊚ | ◯ | ⊚ | X |

|  | No. 8 Comparative Example 2 | No. 9 Comparative Example 3 | No. 10 Comparative Example 4 | No. 11 Comparative Example 5 | No. 12 Comparative Example 6 | No. 13 Comparative Example 7 |
|---|---|---|---|---|---|---|
| Hot-melt adhesive application width (mm) | 2 | 6 | 6 | 6 | 10 | 10 |

TABLE 1-continued

| Hot-melt adhesive application interval (mm) | 10 | 2 | 4 | 6 | 6 | 10 |
|---|---|---|---|---|---|---|
| Results of observation of pleat formation status | Δ | X | X | Δ | Δ | Δ |

◉: Pleats were formed very tidily.
○: Pleats were formed tidily.
Δ: Pleats were formed but not tidily.
X: Formation of pleats was not sufficient.

It can be seen from the results that desirable results can be obtained when the application width of the hot-melt adhesive (specifically, width direction dimension of the sheet joined section) is 0.5 to 4 mm and the application interval of the hot-melt adhesive (specifically, spacing between adjacent sheet joined sections) is 4 to 8 mm.

<Experiment 2>

Sample No. 14 of the stretch sheet was prepared in a manner similar to Experiment 1 (however, the application width of the hot-melt adhesive was 2 mm and the application interval was 6 mm).

Sample No. 15 was prepared in a manner similar to sample No. 14, except that a direction in which the hot-melt adhesive continues was the MD direction of the first sheet material and the second sheet material and a direction of rubber threads was the CD direction of the first sheet material and the second sheet material.

Then, in samples No. 14 and No. 15 of natural length, by aligning a center of a pressure plate, to be described below, with an apex position of the pleats for pleats at five locations, compression characteristics (compression stiffness LC, compression energy WC, compression resilience RC, initial thickness T0, thickness TM at maximum load) were measured, and averages were calculated. Note that the compression stiffness LC indicates that compression is rigid as it is closer to 1. The compression energy WC indicates that the larger the value is, the more easily the sample was compressed. The compression resilience RC indicates that the closer to 100 the value is, the better restorability to compression is. The initial thickness T0, the compression stiffness LC, the compression energy WC, and the compression resilience RC were measured using KES-FB3-AUTO-A automated compression tester based on KES (Kawabata's Evaluation System for Fabrics). Measurements took place during time from when a specimen was compressed between steel pressure plates having a circular plane of compression area of 2 cm$^2$ from 0 gf/cm$^2$ to the maximum compression load 50 gf/cm$^2$, till the specimen was restored. The initial thickness T0 is thickness of the specimen at pressure of 0.5 gf/cm$^2$. The compression stiffness LC represents linearity of compression displacement, and a specimen whose load and displacement (decrease in thickness due to compression) are proportional has a large value. The compression energy WC represents workload of compression, and the larger a numeric value is, the better fullness and stiffness are. The compression resilience represents compression resilience and the larger a value is, the smaller hysteresis is.

TABLE 2

|  |  | Sample No. 14 Example 7 | Sample No. 15 Example 8 |
|---|---|---|---|
| LC | (—) | 1.15 | 0.91 |
| WC | (gfcm/cm$^2$) | 1.63 | 2.00 |
| RC | (%) | 53.3 | 42.7 |
| T0 | (mm) | 6.44 | 6.18 |
| TM | (mm) | 3.60 | 1.78 |
| T0 − TM | (mm) | 2.83 | 4.40 |
| INT | (—) | 16.3 | 20.0 |
| B-INT | (—) | 8.68 | 8.54 |
| GAP | (mm) | 7.02 | 6.62 |

In addition, these samples No. 14 and No. 15 in a state in which they were stretched 1.65 times in the MD direction (assuming a state in which the diaper is worn) were microscope photographed from sides (magnification of 30 times). Based on the photograph results, apparent height 80Y and width 80X of the sample pleats were measured for each pleat 80 to calculate averages. FIG. 14 illustrates photographs and table 3 shows the pleat height and width. KEYENCE digital microscope VHX-1000 was used in the microscope shooting.

TABLE 3

|  |  | Sample No. 14 Example 7 | Sample No. 15 Example 8 |
|---|---|---|---|
| Height | (μm) | 4637 | 4467 |
| Width | (μm) | 3734 | 3008 |

It can be seen from these results that when bending resistance of non-woven fabric in the width direction is set higher than that in the direction orthogonal to the width direction, the pleats not only easily swell roundly and have rich compression resilience in the thickness direction, but also do not easily lie down and yet have softness when touched.

<Experiment 3>

The same first sheet material, the resilient and elastic members, and the second sheet material as Experiment 1 as well as various types of hot-melt adhesives that differ in the melt viscosity and loop tack adhesion were prepared. In equipment similar to that illustrated in FIG. 19, an adhesion test was carried out at line speed of 187 m/min to evaluate operation stability such as stringiness of the hot-melt adhesives or the like on the following two scales:
○: No stringiness was observed and bonding was carried out in a stable manner.
x: Stringiness was observed, precision of the application width was poor, and there was a problem in terms of the operation stability.

TABLE 4

| | | Types of hot-melt adhesives | | | | |
|---|---|---|---|---|---|---|
| | | A | B | C | D | E |
| Melt viscosity (mpas) | 140 °C | 4030 | 6030 | 6900 | 17500 | 21500 |
| | 160 °C | 1750 | 2950 | 3000 | 7080 | 8100 |
| Loop tack | (g/25 mm) | 2710 | 2550 | 1560 | 980 | 40 |
| Evaluation | | ○ | ○ | X | X | X |

It can be seen from the results that desirable results can be obtained if a hot-melt adhesive having the melt viscosity of 10000 mpas or less at temperature of 140° C. and the melt viscosity of 5000 mpass or less at temperature of 160° C., and the loop tack adhesion of 2000 g/25 mm or more is used.

<Descriptions of the Terms Used Herein>

Unless otherwise specified herein, the terms used herein have the meanings described below.

(Gel Strength)

The gel strength is measured in such a manner as described below. That is, a high-absorbent polymer of 1.0 g is added to an artificial urine of 49.0 g (urea: 20 wt %, salt: 8 wt %, calcium chloride dihydrate: 0.3 wt %, magnesium oxide heptahydrate: 0.8 wt %, and pure water: 70.01 wt %), and then the mixture is agitated with a stirrer. The resultant gel is left stand for three hours in a constant temperature and humidity chamber at 40° C. and 60% RH, and then returned to a room-temperature environment. Then, the gel strength is measured by a curd meter (Curdmeter-MAX ME-500 produced by I. Techno Engineering Co., Ltd.).

(Basis Weight)

The basis weight is measured as described below. A specimen or a test piece is preliminarily dried and left stand in a test room or a test device in a standard state (a place of test shall be at a temperature of 20±5° C. and a relative humidity of 65% or less) until reaching a constant weight. The preliminary drying refers to turning the specimen or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) specimen by the use of a basis weight plate (200 mm×250 mm±2 mm). The weight of the specimen is measured and the measured value is multiplied by 20 to determine the weight per square meter as a basis weight.

(Thickness)

The thickness is automatically measured by an automated thickness gauge (KES-G5 handy compression measurement program) on the conditions that the load is 10 gf/cm² and the pressure area is 2 cm².

If there is no description on environmental conditions in testing or measurements, the testing or the measurements shall be conducted in a test room or within a device under a normal state (a place of test shall be at temperatures of 20±5° C. and relative humidity of 60% or less).

INDUSTRIAL APPLICABILITY

The present invention can be applied to underpants-type disposable diapers, in general.

REFERENCE SIGN LIST

11 Liquid impervious sheet
12 Outer body
12A Side seal portion
12H Second sheet material
12S First sheet material
12r Folded part
200 Inner body
30 Top sheet
40 Intermediate sheet
50 Absorbent element
56 Absorber
58 Wrapping sheet
60 Three-dimensional gather
62 Gather sheet
70 Sheet joined section
71 Adhesive
80 Pleat
21 Inner layer
22 Outer layer
F Front panel
B Back panel
WO Waist opening
LO Leg opening
T Waist portion
U Lower waist portion
W Waist edge portion
L Intermediate portion
17 Waist edge portion resilient and elastic member
15 Lower waist portion resilient and elastic member
16 Intermediate portion resilient and elastic member
25 Area not being joined and not having resilient and elastic member

The invention claimed is:

1. An underpants-type disposable diaper, including:
an outer body constituting a front panel and a back panel, and an inner body that includes an absorber and is fixed to the inner surface of the outer body, wherein
the front panel of the outer body and the back panel of the outer body are joined together at the both sides to form side seal portions, thereby forming an annular waist portion and a waist opening and a pair of right and left leg openings,
a waist edge portion of the outer body includes a plurality of elongated waist edge portion resilient and elastic members provided along a width direction and separated from each other, an inner layer composed of a sheet material facing the inside of the waist edge portion resilient and elastic members, and an outer layer composed of a sheet material facing the outside of the waist edge portion resilient and elastic members,
the inner layer and the outer layer are joined by an adhesive arranged intermittently or a welding process performed intermittently in the width direction continuously in a direction crossing the width direction, thereby forming sheet joined sections,
the waist edge portion resilient and elastic members are fixed to at least one of the inner layer and the outer layer at positions intersecting with the sheet joined sections,
the inner layer and the outer layer contracting as the waist edge portion resilient and elastic members contract, portions positioned between the sheet joined sections in the inner layer and the outer layer swell inversely to each other, thus respectively forming pleats, and
the diaper includes an area not being joined and not having resilient and elastic member at an end portion of the outer body on the waist opening side in the waist edge portion, the area not having sheet joined sections nor the waist edge portion resilient and elastic members, and a vertical range being wider than spacing between the waist edge portion resilient and elastic member positioned closest to the waist opening side, and the waist edge portion resilient and elastic member adjacent thereto.

2. The underpants-type disposable diaper according to claim 1, wherein distance from the edge of the waist opening to a forward end of the sheet joined section on the waist opening side is 3 to 15 mm, and distance from the edge of the waist opening to the waist edge portion resilient and elastic member positioned closest to the waist opening side is 5 to 20 mm.

3. The underpants-type disposable diaper according to claim 1, wherein the area not being joined and not having resilient and elastic member has a structure of three or more layers, by folding back at least one of the sheet material constituting the inner layer and the sheet material constituting the outer layer at the waist opening.

4. The underpants-type disposable diaper according to claim 1, wherein the inner layer and the outer layer are respectively formed by a portion positioned inside and a portion positioned outside one sheet material, which is folded at the waist opening.

5. The underpants-type disposable diaper according to claim 1, wherein
the sheet joined sections are formed by the adhesive,
on the inner layer side and the outer layer side of the waist edge portion resilient and elastic members in parts where the sheet joined sections intersect with the waist edge portion resilient and elastic members, the adhesive is continuous in the direction crossing the width direction, thereby fixing the waist edge portion resilient and elastic members to the inner layer and the outer layer with the adhesive.

6. The underpants-type disposable diaper according to claim 1, wherein dimension of each sheet joined section in the width direction is 0.5 to 4 mm, and spacing of adjacent sheet joined sections in the width direction is 4 to 8 mm.

7. The underpants-type disposable diaper according to claim 1, wherein spacing of the adjacent waist edge portion resilient and elastic members is 10 mm or less.

8. The underpants-type disposable diaper according to claim 1, wherein each of the inner layer and the outer layer is non-woven fabric having thickness of 0.1 to 1 mm and basis weight of 10 to 20 g/m2.

9. The underpants-type disposable diaper according to claim 1, wherein an extension ratio of the waist edge portion resilient and elastic members when the waist edge portion is completely unfolded in the width direction is 200 to 350%.

10. The underpants-type disposable diaper according to claim 1, wherein the inner layer and the outer layer are non-woven fabric whose bending resistance in the width direction is higher than that in the direction orthogonal to the width direction.

* * * * *